(12) United States Patent
Yoon et al.

(10) Patent No.: US 11,767,318 B2
(45) Date of Patent: Sep. 26, 2023

(54) CATHODE BUFFER LAYER MATERIAL AND ORGANIC PHOTOELECTRIC DEVICE INCLUDING SAME

(71) Applicant: KOREA RESEARCH INSTITUTE OF CHEMICAL TECHNOLOGY, Daejeon (KR)

(72) Inventors: Sung Cheol Yoon, Daejon (KR); Chang Jin Lee, Daejeon (KR); Jaemin Lee, Daejeon (KR); Seung Hun Eom, Jeonju-si (KR)

(73) Assignee: Korea Research Institute of Chemical Technology, Daejeon (KR)

( * ) Notice: Subject to any disclaimer, the term of this patent is extended or adjusted under 35 U.S.C. 154(b) by 548 days.

(21) Appl. No.: 16/642,849

(22) PCT Filed: Jul. 17, 2018

(86) PCT No.: PCT/KR2018/008084
§ 371 (c)(1),
(2) Date: Feb. 27, 2020

(87) PCT Pub. No.: WO2019/045269
PCT Pub. Date: Mar. 7, 2019

(65) Prior Publication Data
US 2021/0032237 A1  Feb. 4, 2021

(30) Foreign Application Priority Data
Aug. 28, 2017 (KR) .................. 10-2017-0108921

(51) Int. Cl.
*C07D 455/06* (2006.01)
*C07C 229/44* (2006.01)
*C07C 255/43* (2006.01)
*H10K 30/81* (2023.01)
*H10K 85/60* (2023.01)

(52) U.S. Cl.
CPC .......... *C07D 455/06* (2013.01); *C07C 229/44* (2013.01); *C07C 255/43* (2013.01); *H10K 30/81* (2023.02); *H10K 85/6572* (2023.02)

(58) Field of Classification Search
CPC .................................................. H01K 30/81
See application file for complete search history.

(56) References Cited

FOREIGN PATENT DOCUMENTS

| JP | 2005-019251 | | 1/2005 |
|----|----|----|----|
| JP | 2007149570 A | * | 6/2007 |
| JP | 2011-238905 | | 11/2011 |
| JP | 2013-079315 | | 5/2013 |
| JP | 2014-130250 | | 7/2014 |
| KR | 10-2003-0026984 | | 4/2003 |
| KR | 10-2010-0066115 | | 6/2010 |
| KR | 10-2015-0136112 | | 12/2015 |

OTHER PUBLICATIONS

Choi "Development of a julolidine-based interfacial modifier for efficient inverted polymer solar cells" RSC Adv., 2015, 5, 107540-107546.*
Eom "Roles of Interfacial Modifiers in Hybrid Solar Cells: Inorganic/Polymer Bilayer vs Inorganic/Polymer:Fullerene Bulk Heterojunction" ACS Appl. Mater. Interfaces 2014, 6, 803-810.*
International Search Report in PCT /KR2018/000804, dated Jul. 5, 2018.
E. Y. Choi, et al., Development of Julolidine-based Interfacial Modifier for Efficient Inverted Polymer Solar Cells, Article, ed, RSC Adv., 2015, 1-8, United Kingdom.

* cited by examiner

*Primary Examiner* — David K O'Dell
(74) *Attorney, Agent, or Firm* — WORKMAN NYDEGGER

(57) ABSTRACT

The present invention relates to a novel cathode buffer layer material and an organic photoelectric device including the same. When the novel compound of the present invention is applied to a cathode buffer layer of an organic photoelectric device, for example, an organic solar cell or an organic photodiode, there is an effect in which the surface characteristics of an electron transport layer are improved through the high dipole moment of the novel compound to thereby facilitate electron extraction from a photoactive layer to a cathode electrode and to reduce series resistance and leakage current, and accordingly, the performance of an organic optoelectronic device (organic solar cell, organic photodiode, etc.) to be manufactured can be remarkably improved, which is industrially advantageous.

8 Claims, 7 Drawing Sheets

【Figure 1】
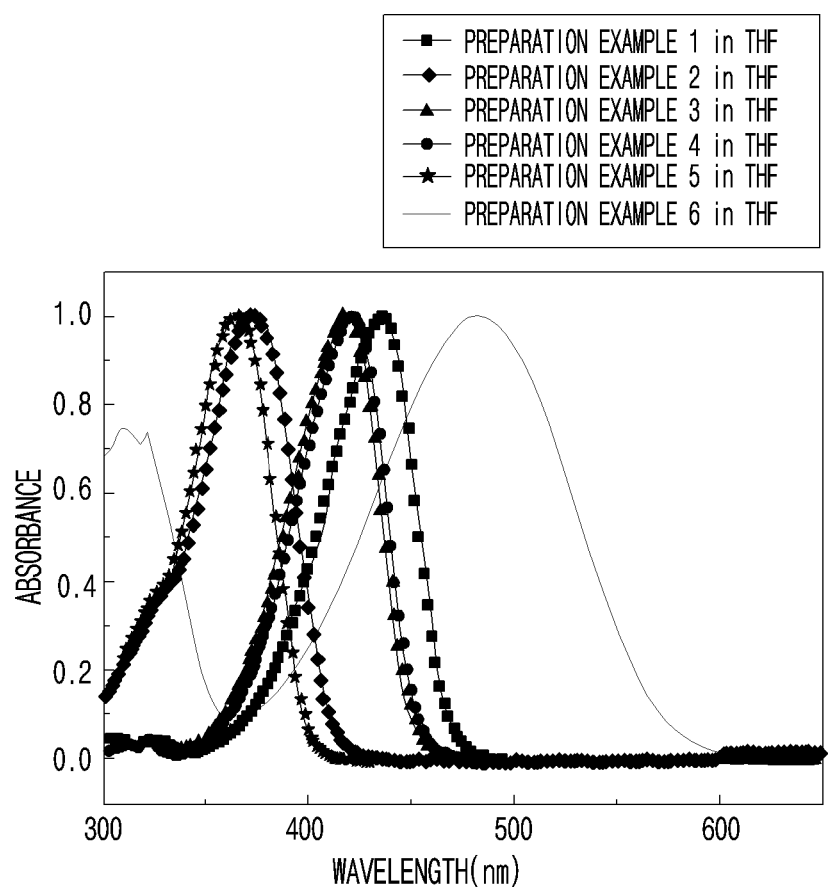

[Figure 2]
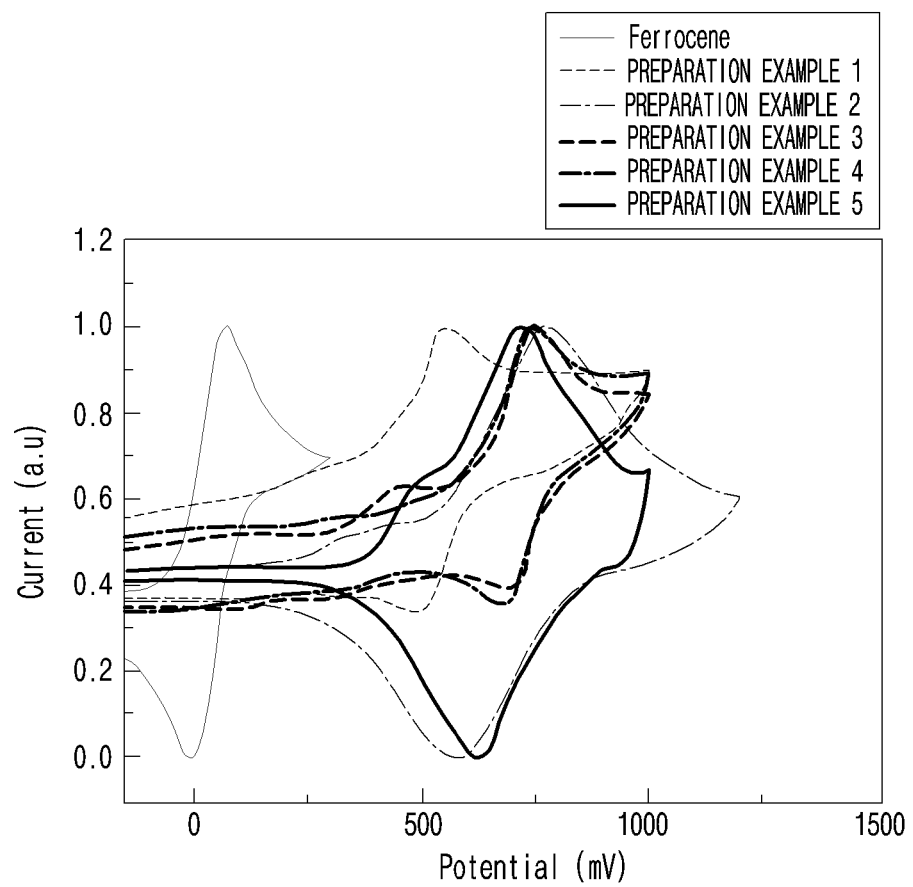

[Figure 3]
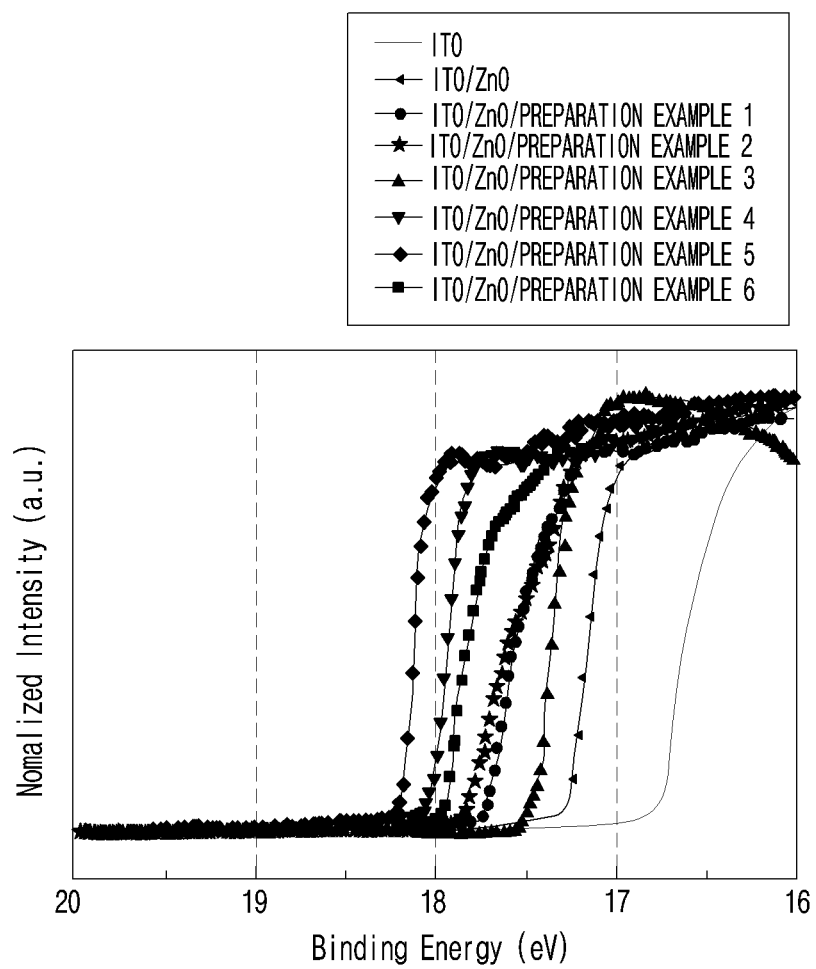

[Figure 4]
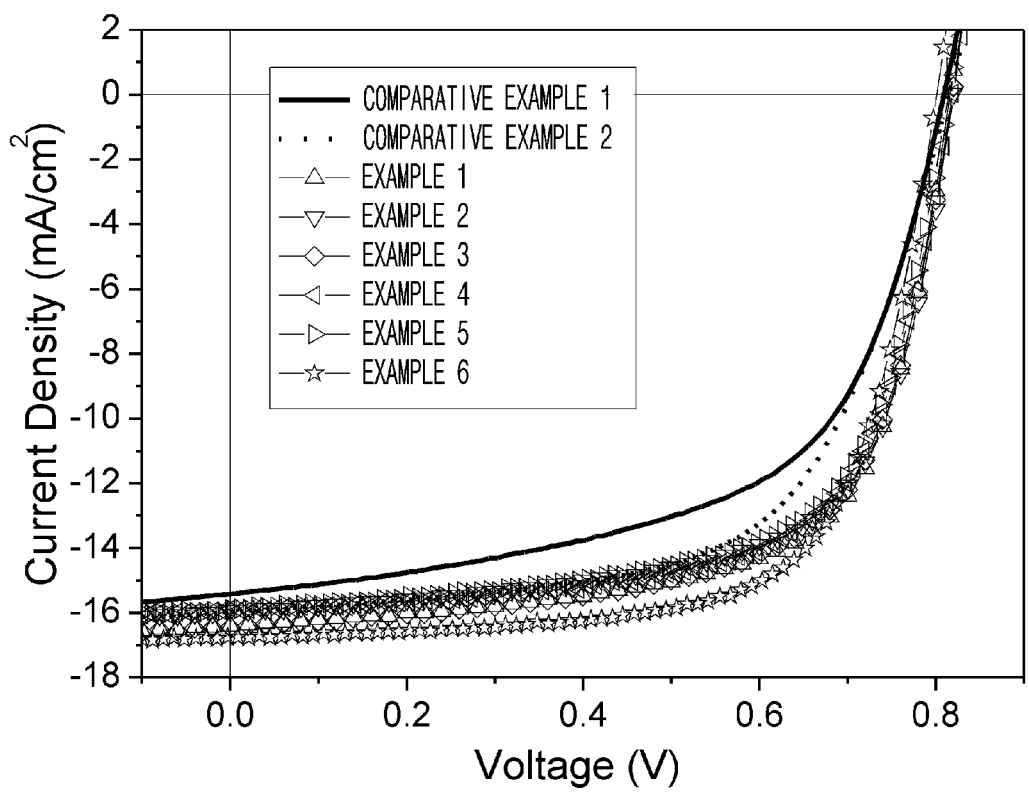

[Figure 5]
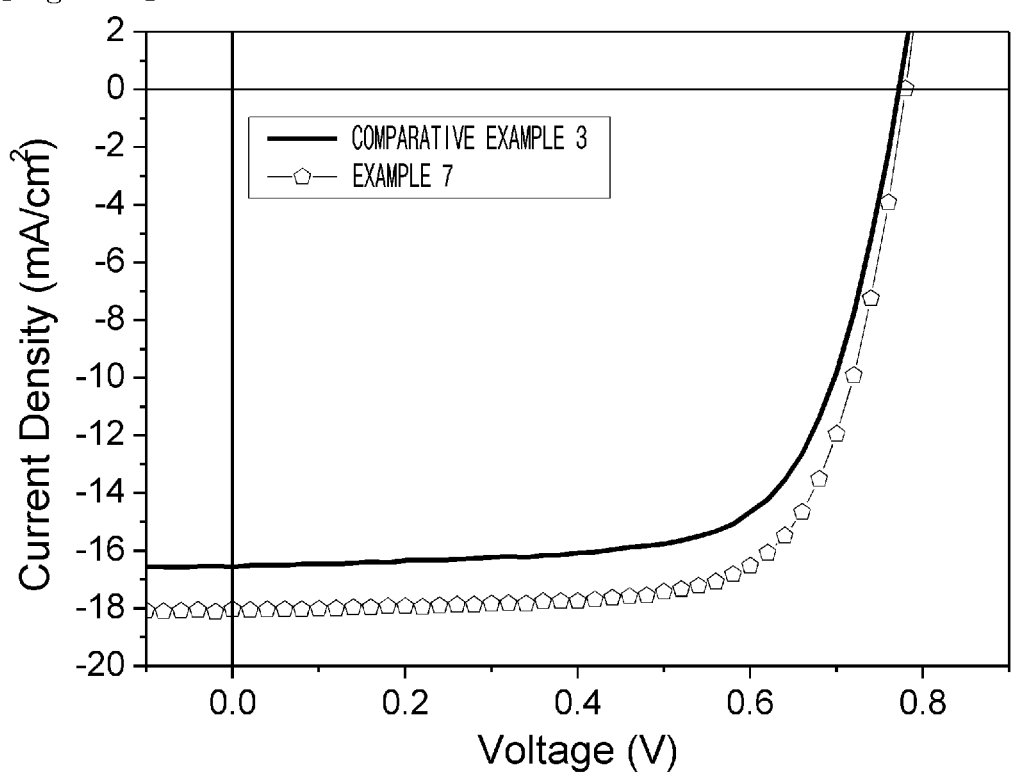

[Figure 6]
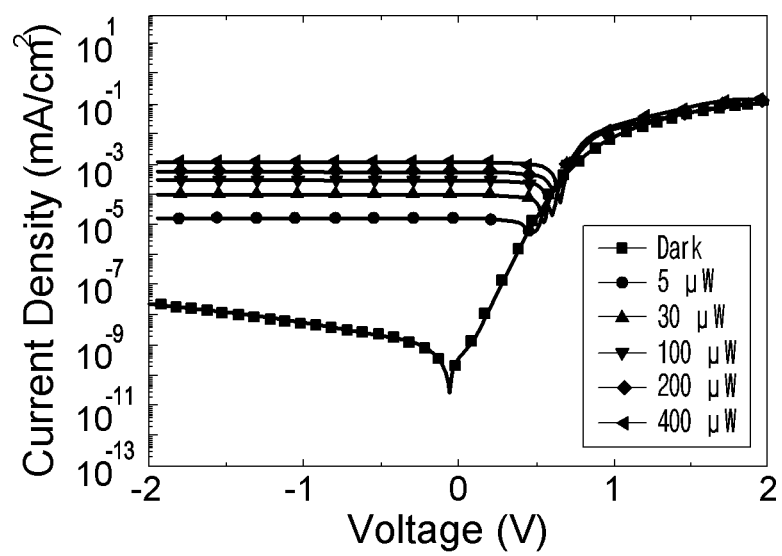

【Figure 7】
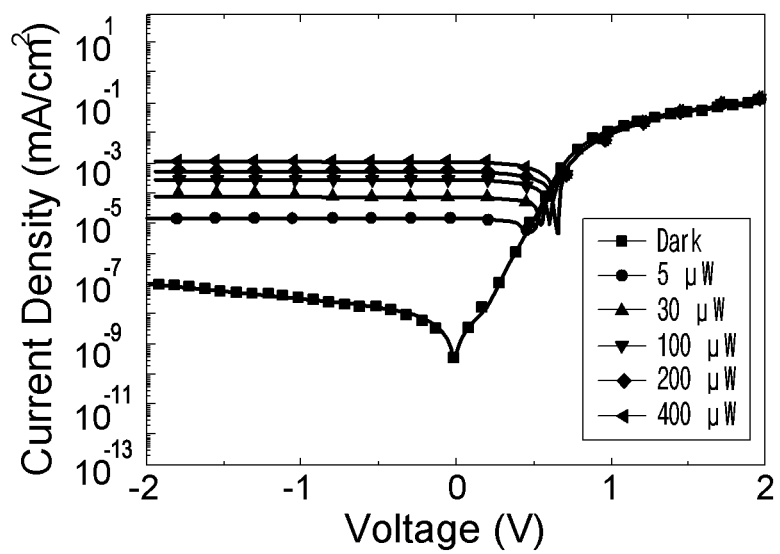

CATHODE BUFFER LAYER MATERIAL AND ORGANIC PHOTOELECTRIC DEVICE INCLUDING SAME

CROSS-REFERENCE TO RELATED APPLICATIONS

This application claims priority to PCT Application No. PCT/KR2018/008084 filed Jul. 17, 2018, entitled "NOVEL CATHODE BUFFER LAYER MATERIAL AND ORGANIC PHOTOELECTRIC DEVICE INCLUDING SAME," which claims the benefit of and priority to Korean Patent Application No. 10-2017-0108921, filed on Aug. 28, 2017, all of which are incorporated herein by reference in their entirety.

TECHNICAL FIELD

The present invention relates to a novel cathode buffer layer material and an organic photoelectric device including same.

BACKGROUND ART

Electronic devices have a basic structure of two electrodes and an active layer disposed therebetween, and a typical layer configuration with an additional charge transport layer disposed between electrodes or between an electrode and an active layer. In this case, the issue on the interlayer adhesion between the active layer and the charge (electron, hole) transport layer or between electrodes is one of technical tasks from the initial stage of development, because the interlayer adhesion becomes an important factor as much as the configuration of the material itself of each layer in securing the performance of a device.

The easiest way relating to the interlayer adhesion is a method of adding a third material to a material used as the charge transport layer such as PEDOT:PSS. For example, there are a charge transport layer material using the material used as the charge transport layer such as PEDOT:PSS together with a polymer having conductivity and a polar functional group as a side chain substituent such as a sulfonated polystyrene, and a compound represented by the general formula of (HO)n-R—(COX)m as a material which may be used by blending with PEDOT, for example, sugar derivatives, ethylene glycol, or triethylene glycol, or the like.

As another attempt for the interlayer adhesion, a separate adhesion layer is disposed in the conventional interlayer configuration. For example, in an organic photoelectric device having a typical layer configuration composed of ITO/PEDOT:PSS/P3HT and PCBM/aluminum, an interface layer formed from the derivative of a carboxylic acid anhydride such as pyromellitic acid dianhydride and trimellitic acid anhydride may be disposed between an electrode and an active layer or a charge transport layer and an active layer.

In addition, in case of an organic photoelectric device having a reverse structure, which is suitable for a printing process, an ink of a metal having a high work function such as gold, silver and platinum is inevitably used as an upper electrode for printing the upper electrode suitable for a printing process, but aluminum in the conventional organic photoelectric device having a normal structure is easily oxidized and is inappropriate for a printing process, and accordingly, the used thereof is limited. Accordingly, in order to decrease the high work function of ITO which is used as a transparent electrode, a thin film such as ZnO and TiO2 is formed on the ITO layer and used. However, the interface properties of such metal oxide-based cathode buffer materials with an organic photoactive layer are degraded, and there are problems of decreasing the shunt resistance and a fill factor (FF) of a device (RSC Adv., 2015, 5, 107540-107546).

In addition, such degradation of the interface properties between an inorganic buffer layer and an organic photoactive layer elevates the leakage current of an organic photodiode and acts as a factor degrading the detectivity and stability of a device, and accordingly, the commercialization of an organic photodiode device for a solution process is delayed.

Accordingly, the present inventors tried to solve the problems of the conventional related arts by providing a novel organic material which may easily control the interface between a metal oxide-based cathode buffer material and a photoactive layer, as a result, ascertained that the performance of an organic photoelectric device, for example, an organic solar cell and an organic photodiode is improved by using the compound or the preparation example of the present invention as a buffer layer material, and completed the present invention.

DISCLOSURE OF THE INVENTION

Technical Problem

One object of the present invention is to provide a novel cathode buffer layer material.

Another object of the present invention is to provide a method of preparing the novel cathode buffer layer material.

Still another object of the present invention is to provide an organic photoelectric device including the novel cathode buffer layer material.

Even another object of the present invention is to provide an organic solar cell including the novel cathode buffer layer material.

Yet another object of the present invention is to provide an organic photodiode including the novel cathode buffer layer material.

Technical Solution

In order to achieve the objects, the present invention provides a compound represented by the following Formula 1, or stereoisomers thereof:

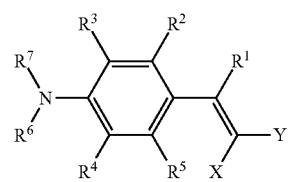

[Formula 1]

at least one of X and Y is $CO_2H$, where if X is $CO_2H$, Y is hydrogen or CN, and if Y is $CO_2H$, X is hydrogen or CN;

$R^1$ is hydrogen, substituted or unsubstituted $C_{1-10}$ linear or branched alkyl, or substituted or unsubstituted $C_{1-10}$ linear or branched alkoxy, where the substituted alkyl and the substituted alkoxy may be substituted with one or more substituents selected from the group consisting of $C_{1-5}$ linear or branched alkyl, and $C_{1-5}$ linear or branched alkoxy;

$R^2$ to $R^5$ are each independently H, OH, halogen, substituted or unsubstituted amino, or substituted or unsubstituted $C_{1-5}$ linear or branched alkyl, where the substituted amino, and the substituted alkyl may be substituted with one or more substituents selected from the group consisting of OH, halogen, $C_{1-5}$ linear or branched alkyl, and an amino group; and $R^6$ and $R^7$ are each independently H, substituted or unsubstituted $C_{1-20}$ linear or branched alkyl, substituted or unsubstituted $C_{2-20}$ linear or branched unsaturated alkyl including one or more double bonds or triple bonds, substituted or unsubstituted $C_{3-10}$ cycloalkyl, substituted or unsubstituted heterocycloalkyl with a triangular to decagonal ring, including one or more heteroatoms selected from the group consisting of N, O and S, substituted or unsubstituted $C_{6-10}$ aryl, or substituted or unsubstituted heteroaryl with a pentagonal to decagonal ring, including one or more heteroatoms selected from the group consisting of N, O and S, or $R^6$ may form a substituted or unsubstituted heterocycle with a pentagonal to decagonal ring together with an N atom connected with $R^6$ and $R^4$, and $R^7$ may form a substituted or unsubstituted heterocycle with a pentagonal to decagonal ring together with an N atom connected with $R^7$ and $R^3$, where the substituted alkyl, substituted unsaturated alkyl, substituted cycloalkyl, substituted heterocycloalkyl, substituted aryl, substituted heterocycle and substituted heteroaryl may be substituted with one or more substituents selected from the group consisting of OH, halogen, $C_{1-5}$ linear or branched alkyl, and an amino group.

In addition, the present invention provides a method of preparing the compound represented by Formula 1, including:

a step of preparing a compound represented by Formula 3 from a compound represented by Formula 2; and a step of preparing the compound represented by Formula 1 from the compound represented by Formula 3, as shown in the following Reaction 1:

[Reaction 1]

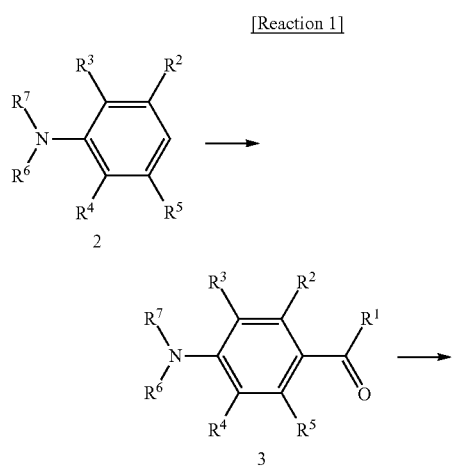

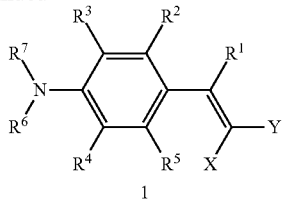

(in Reaction 1,

X, Y, $R^1$, $R^2$, $R^3$, $R^4$, $R^5$, $R^6$, and $R^7$ are the same as defined in Formula 1).

Furthermore, the present invention provides a composition for a cathode buffer layer, including the compound represented by Formula 1 or stereoisomers thereof.

In addition, the present invention provides a cathode buffer layer including the compound or stereoisomers thereof; and one or more cathode buffer materials selected from an n-type metal oxide, a transition metal chelate, and an alkali metal compound.

Furthermore, the present invention provides an organic solar cell including the cathode buffer.

Furthermore, the present invention provides an organic photodiode including the cathode buffer layer.

Advantageous Effects

When the novel compound of the present invention is applied to a cathode buffer layer of an organic photoelectric device, for example, an organic solar cell or an organic photodiode, there is an effect in which the surface characteristics of an electron transport layer are improved through the high dipole moment of the novel compound to thereby facilitate electron extraction from a photoactive layer to a cathode electrode and to reduce series resistance and leakage current, and accordingly, the performance of an organic photoelectric device (organic solar cell, organic photodiode, etc.) to be manufactured may be remarkably improved, which is industrially advantageous.

BRIEF DESCRIPTION OF THE DRAWINGS

FIG. 1 is a graph showing the UV/Vis absorption spectrum of the compounds of Preparation Examples 1-6.

FIG. 2 is a cyclic voltammetry (CV) graph of the compounds of Preparation Examples 1-6.

FIG. 3 is a graph showing the UPS measurement results of ITO, ITO/ZnO, and ITO/ZnO/compound layers of Preparation Examples 1-6.

FIG. 4 is a current density (mA/cm$^2$)-voltage (V) graph of the devices of Examples 1-6 and Comparative Examples 1-2, in which a PTB7-Th:PC70BM photoactive layer is applied.

FIG. 5 is a current density (mA/cm$^2$)-voltage (V) graph of the devices of Example 7 and Comparative Example 3, in which a PPDT2FBT:PC90BM photoactive layer is applied.

FIG. 6 is a current density (mA/cm$^2$)-voltage (V) graph between −2 V to +2 V in accordance with the light intensity change of the device of Example 8, in which a PTB-7:PC70BM photoactive layer is applied, a ZnO layer is formed, and the compound layer of Preparation Example 1 of the present invention is introduced.

FIG. 7 is a current density (mA/cm$^2$)-voltage (V) graph between −2 V to +2 V in accordance with the light intensity change of the device of Comparative Example 4, in which a PTB-7:PC70BM photoactive layer is applied, and a ZnO single layer of the present invention is manufactured as a cathode buffer layer.

MODE FOR CARRYING OUT THE INVENTION

Hereinafter, the present invention will be explained in detail.

The present invention provides a compound represented by the following Formula 1, or stereoisomers thereof:

[Formula 1]

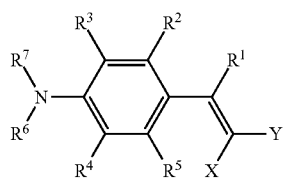

in Formula 1, at least one of X and Y is $CO_2H$, where if X is $CO_2H$, Y is hydrogen or CN, and if Y is $CO_2H$, X is hydrogen or CN;

$R^1$ is hydrogen, substituted or unsubstituted $C_{1-10}$ linear or branched alkyl, or substituted or unsubstituted $C_{1-10}$ linear or branched alkoxy, where the substituted alkyl and the substituted alkoxy may be substituted with one or more substituents selected from the group consisting of $C_{1-5}$ linear or branched alkyl, and $C_{1-5}$ linear or branched alkoxy;

$R^2$ to $R^5$ are each independently H, OH, halogen, substituted or unsubstituted amino, or substituted or unsubstituted $C_{1-5}$ linear or branched alkyl, where the substituted amino, and the substituted alkyl may be substituted with one or more substituents selected from the group consisting of OH, halogen, $C_{1-5}$ linear or branched alkyl, $C_{1-5}$ linear or branched alkoxy, oxo, and an amino group; and $R^6$ and $R^7$ are each independently H, substituted or unsubstituted $C_{1-20}$ linear or branched alkyl, substituted or unsubstituted $C_{2-20}$ linear or branched unsaturated alkyl including one or more double bonds or triple bonds, substituted or unsubstituted heterocycloalkyl with a triangular to decagonal ring, including one or more heteroatoms selected from the group consisting of N, O and S, substituted or unsubstituted $C_{6-10}$ aryl, or substituted or unsubstituted heteroaryl with a pentagonal to decagonal ring, including one or more heteroatoms selected from the group consisting of N, O and S, or $R^6$ and $R^7$ may be each independently, $R^6$ may form a substituted or unsubstituted heterocycle with a pentagonal to decagonal ring together with an N atom connected with $R^6$ and $R^4$, and $R^7$ may form a substituted or unsubstituted heterocycle with a pentagonal to decagonal ring together with an N atom connected with $R^7$ and $R^3$, or $R^6$ and $R^7$ may form substituted or unsubstituted hyterocycloalkyl with a triangular to decagonal ring together with an N atom connected therewith, where the substituted alkyl, substituted alkoxy, substituted unsaturated alkyl, substituted cycloalkyl, substituted heterocycloalkyl, substituted aryl, substituted heterocycle and substituted heteroaryl may be substituted with one or more substituents selected from the group consisting of OH, halogen, cyano, nitro, $C_{1-5}$ linear or branched alkyl, $C_{1-5}$ linear or branched alkoxy, oxo, and an amino group.

According to an aspect of the present invention, $R^6$ and $R^7$ may be each independently H, $C_{1-20}$ linear or branched alkyl, or $R^6$ and $R^7$ may be each independently, $R^6$ may form a substituted or unsubstituted heterocycle with a pentagonal to decagonal ring together with an N atom connected with $R^6$ and $R^4$, and $R^7$ may form a substituted or unsubstituted heterocycle with a pentagonal to decagonal ring together with an N atom connected with $R^7$ and $R^3$, where the substituted heterocycle may be substituted with one or more substituents selected from the group consisting of $C_{1-5}$ linear or branched alkyl.

In a particular embodiment of the present invention, if $R^6$ and $R^7$ are each independently $C_{1-6}$ linear or branched alkyl, X is $CO_2H$, and Y is H or CN.

In another particular embodiment of the present invention, if $R^6$ and $R^7$ are each independently $C_{7-10}$ linear or branched alkyl, Y is $CO_2H$, and X is H or CN.

In another particular embodiment, if $R^6$ forms a substituted or unsubstituted heterocycle with a pentagonal to decagonal ring together with an N atom connected with $R^6$ and $R^4$, and $R^7$ forms a substituted or unsubstituted heterocycle with a pentagonal to decagonal ring together with an N atom connected with $R^7$ and $R^3$, Y is $CO_2H$, and X is H or CN.

According to another aspect of the present invention, $R^6$ and $R^7$ may be each independently H, $C_{1-20}$ linear or branched alkyl, or $R^6$ and $R^7$ may be each independently, $R^6$ may form

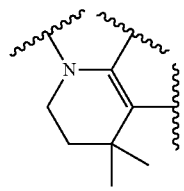

together with an N atom connected with $R^6$ and $R^4$, and $R^7$ may form

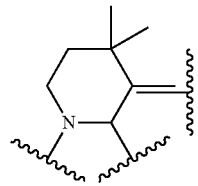

together with an N atom connected with $R^7$ and $R^3$.

In another particular embodiment, the compound represented by Formula 1 may be 0

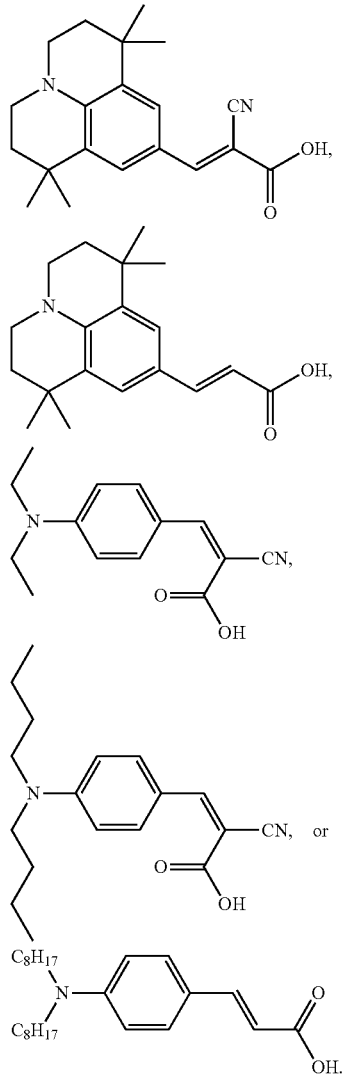

Meanwhile, in a particular embodiment of the present invention, the compound of Formula 1 may be one among the compounds having the following compound names:

(1) (E)-2-cyano-3-(1,1,7,7-tetramethyl-2,3,6,7-tetrahydro-1H,5H-pyrido[3,2,1-ij]quinolin-9-yl)acrylic acid;
(2) (Z)-2-cyano-3-(4-(diethylamino)phenyl)acrylic acid;
(3) (Z)-2-cyano-3-(4-(diethylamino)phenyl)acrylic acid;
(4) (Z)-2-cyano-3-(4-(dibutylamino)phenyl)acrylic acid; and
(5) (E)-3-(4-(dioctylamino)phenyl)acrylic acid.

In an aspect of the present invention, the compound represented by Formula 1 or stereoisomers thereof are molecules having high dipole moment, and a dialkylamino phenyl moiety and a cyanoacrylic acid moiety, which are the terminal moieties of the compound, may be understood as a hydrophobic donor and a hydrophilic acceptor, respectively.

The compound of the present invention or stereoisomers thereof may form a double layer with the conventional metal oxide-based cathode buffer and a photoactive layer, or may be dispersed in the conventional metal oxide-based cathode buffer material. Particularly, by forming a high dipole moment layer at an interface, effects of easily transporting electrons produced in a photoactive layer to a cathode electrode may be achieved.

Further, the compound of the present invention or stereoisomers thereof may be used in a composition for a cathode buffer layer and applied to the cathode buffer layer of an organic photoelectric device, for example, an organic solar cell and an organic photodiode, and as a result, remarkable effects such as the efficiency improvement of a device and device stability improvement may be shown.

In a particular embodiment, the organic solar cell devices of Examples 1-7, manufactured by applying the compounds of Preparation Examples 1-5 of the present invention have, without limitation, PTB7-Th:PC70BM, or PPDT2FBT:PC70BM as a photoactive layer, and use ZnO as a cathode buffer material. A method of forming one layer between the two layers to form a cathode buffer layer into a double layer of ZnO/the compound of the present invention, or a method of forming a single cathode buffer layer by mixing with a cathode buffer material and forming a layer using the solution thus obtained, may be applied to the organic solar cell devices.

In another aspect of the present invention, if an organic photoelectric device is manufactured by the method of forming a single cathode buffer layer, effects of markedly improved device efficiency and stability may be shown in contrast to the double layer. In addition, the method of forming a single layer has merits of easier application than the forming method of a double layer in a device manufacturing process through a printing method.

Meanwhile, if calculating the dipole moment of the compound molecules of Preparation Examples 1-5 below, which are particular embodiments of the present invention, by a density functional theory (DFT, B3LYP, 6-31G*) method using a Spartan 16 software, the compound molecules of Preparation Examples 1-5 of the present invention have dipole moments, and electron transfer from a photoactive layer to a cathode electrode may be performed more smoothly. Particularly, since the compounds of the present invention as in Preparation Examples 1-5 have a condensed molecular structure, electron transfer may be even more smoothly performed.

In addition, the present invention provides a method of preparing the compound represented by Formula 1, including:

a step of preparing a compound represented by Formula 3 from a compound represented by Formula 2; and a step of preparing the compound represented by Formula 1 from the compound represented by Formula 3, as shown in the following Reaction 1:

[Reaction 1]

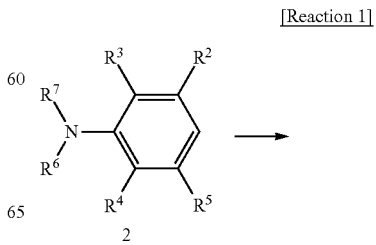

2

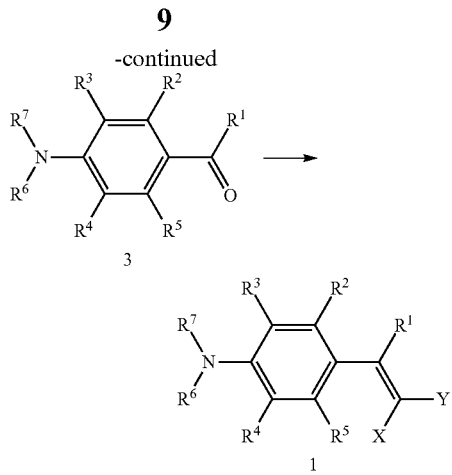

(in Reaction 1,

X, Y, R$^1$, R$^2$, R$^3$, R$^4$, R$^5$, R$^6$, and R$^7$ are the same as defined in Formula 1)

Hereinafter, the preparation method of the compound represented by Formula 1 will be explained in detail step by step.

In the preparation method of the compound represented by Formula 1 according to the present invention, the step preparing a compound represented by Formula 3 from a compound represented by Formula 2 may be understood as a reaction of introducing an aldehyde group to phenyl so that a cyanoacrylic acid moiety which is a hydrophilic acceptor moiety may be introduced into dialkylaminophenyl which is a hydrophobic donor moiety.

In an aspect of the step, the compound represented by Formula 3 which is an aldehyde derivative may be prepared by reacting the compound represented by Formula 2 with, for example, POCl$_3$. Here, solvents used are not specifically limited but may use one selected from the group consisting of diethyl ether, toluene, dimethyl formamide (DMF), tetrahydrofuran (THF), dichloromethane (DCM), and acetonitrile, or a mixture of two or more thereof. In a particular embodiment, DMF may be used.

In addition, in performing the reaction of the step, the reaction time is not specifically limited as long as a product may be produced, but may be 5 to 40 hours, 10 to 30 hours, 20 to 30 hours, or about 24 hours.

Further, the reaction temperature of the step is not specifically limited, but in an aspect, the reaction may be performed at 60 to 90° C., 70 to 90° C., or about 80 to 85° C.

Meanwhile, the compound represented by Formula 2, which is the reactant in the reaction initiation stage of the step may be, for example, aniline, or derivatives thereof, and suitable substituents may be introduced to the amino moiety of aniline considering a compound desired to finally obtain, and the resultant compound may be used as the reactant which is the compound represented by Formula 2 in the step.

In the preparation method of the compound represented by Formula 1 according to the present invention, the step for preparing the compound represented by Formula 1 from the compound represented by Formula 3 is a step of preparing the compound represented by Formula 1, which is a final target compound, i.e., a cathode buffer layer modification compound by finally introducing a hydrophilic donor moiety which is an acrylic acid derivative as the substitution moiety of the aldehyde group of the compound represented by Formula 3.

In an aspect of the step, the reaction is performed by adding, for example, piperidine, to the compound represented by Formula 3, for example, carboxylic acid such as cyanoacetic acid and malonic acid.

Here, the solvent used is not specifically limited but may be one selected from the group consisting of acetonitrile (ACN), chloroform, dimethyl formamide (DMF), tetrahydrofuran (THF), and dimethyl sulfoxide (DMSO), or a mixture of two or more thereof. In a particular embodiment, a mixture of acetonitrile and chloroform may be used.

In addition, in performing the reaction of the step, the reaction time is not specifically limited as long as a product may be produced, but may be 5 to 40 hours, 10 to 30 hours, 12 to 24 hours, or 8 to 20 hours.

Further, the reaction temperature of the step is not specifically limited, but in an aspect, the reaction may be performed at 60 to 90° C., 70 to 90° C., or about 80 to 85° C.

The above-described preparation method may be understood as a preparation method of a particular embodiment of the present invention, and the reaction conditions may be changed, and the above-described preparation method may be modified considering the structure of a target compound, the yield of a product, etc. Since the purposes of the present invention are the compound represented by Formula 1, and the improvement of the efficiency and stability of an organic photoelectric device and an organic solar cell by using the compound, it should be understood that any preparation methods which are capable of preparing the compound of Formula 1 which is intended to provide in the present invention by the above-described preparation method, are included in the scope of the present invention.

Further, the present invention provides a composition for a cathode buffer layer, including the compound represented by Formula 1 or stereoisomers thereof.

In this case, the composition for a cathode buffer layer may be understood to include the compound represented by Formula 1 as a main constituent component, and additional methods and constituent components for increasing charge transfer or electron movement between a cathode electrode and a photoactive layer may be included.

Particularly, in an aspect of the present invention, the composition for a cathode buffer layer may be understood to include the compound represented by Formula 1 of the present invention and a cathode buffer material.

Here, the cathode buffer material may be one or more cathode buffer materials selected from an n-type metal oxide, a transition metal chelate and an alkali metal compound, and in a particular embodiment, one or more selected from the group consisting of ZnO, TiOx, a titanium chelate, a zirconium chelate, LiF, CsF and Cs$_2$CO$_3$ may be used. The conventional well-known cathode buffer materials may be included in the present invention, without limitation.

Particularly, considering that the compound represented by Formula 1 or stereoisomers thereof of the present invention modify the cathode buffer material to act at the interface of the cathode buffer material and a photoactive layer for the easy movement of electrons from a photoactive layer to a cathode electrode, the cathode buffer materials applicable may be included in the cathode material, only if any one among the effects intended to show in the present invention by applying the compound and stereoisomers thereof of the present invention, that is, effects of easy electron transfer, efficiency of an organic photoelectric device and organic solar cell manufactured therefrom, for example, decreasing effects of series resistance and leakage current, improving photoelectric conversion efficiency, improving device stability, etc. is shown, and the cathode buffer materials are also understood to be included in the scope of the present invention.

In addition, the present invention provides a method of preparing a composition for a cathode buffer layer, including a step of preparing a mixture solution by mixing the compound represented by Formula 1 or stereoisomers thereof with a cathode buffer material.

Here, the cathode buffer material refers to the above-explained cathode buffer material, and may be understood as a step of preparing a mixture solution into a solution, for example, a sol-gel solution in preparing the composition.

In the experimental examples below of the present invention, particularly, in forming a cathode buffer layer, the cathode buffer layer is provided by forming separate double layers of the cathode buffer material and the compound or stereoisomers thereof of the present invention, or by mixing the materials as in the above step and forming a layer.

Here, any methods showing the effects of the present invention may be included in the scope of the present invention without distinction of the methods of forming the double layer or the single layer after mixing. In the experimental example below, as a particular embodiment, it is verified that the most improved efficiency of an organic solar cell is shown in an example of mixing a cathode buffer material with the compound of the present invention prior to forming a cathode buffer layer, and accordingly, further improved effects may be achieved in an organic photoelectric device, for example, a solar cell aiming the formation of a cathode buffer layer as a single layer after mixing.

In addition, in respect of manufacturing an organic photoelectric device by a printing process, the method of forming a layer as a single layer after mixing may have excellent merits regarding processing, because the steps of a preparation process may be reduced and simplified when compared with a method of manufacturing a cathode buffer layer as a double layer.

Further, the present invention provides a cathode buffer layer including the compound represented by Formula 1, or stereoisomers thereof; and one or more cathode buffer materials selected from an n-type metal oxide, a transition metal chelate, and an alkali metal compound.

In this case, the cathode buffer material is the same as the cathode buffer material explained in the preparation method of the composition for a cathode buffer layer, and for example, any materials used in a cathode buffer layer provided between the photoactive layer and cathode electrode of an organic photoelectric device may be included in the present invention, without limitation.

Meanwhile, the compound represented by Formula 1 or stereoisomers thereof may be mixed with and dispersed in the cathode buffer material to form a single layer, or may be formed separately as a double layer including a first layer including the cathode material and a second layer including the compound represented by Formula 1 or stereoisomers thereof.

Particularly, in an aspect of the present invention, in an organic photoelectric device, for example, an organic solar cell or an organic photodiode, for another example, a reverse structure organic photoelectric device, for example, a reverse structure organic solar cell, the cathode buffer layer may be applied, and from dipole moment originated from the molecular structure of the compound of Formula 1 or stereoisomers thereof of the present invention, effects of improving performance of properties such as the efficiency and stability of a device may be finally achieved.

In addition, the present invention provides an organic photoelectric device including:
a first electrode;
a second electrode oppositely provided to the first electrode;
a photoactive layer provided between the first electrode and the second electrode; and
the cathode buffer layer of claim 7, provided between the photoactive layer and the first electrode or the second electrode.

Further, the present invention provides an organic solar cell or an organic photodiode including the composition for a cathode buffer layer.

In an aspect of the present invention, it could be understood that any one among the first electrode and the second electrode is an anode electrode, and the other one is a cathode electrode.

In an aspect of the present invention, the organic photoelectric device (organic solar cell, organic photodiode, etc.) may further include a substrate, a hole transport layer and/or an electron transport layer.

In an embodiment of the present invention, the photoactive layer includes a hole transport layer, a hole injection layer, or a layer transporting holes and injecting holes simultaneously.

In another embodiment of the present invention, the photoactive layer includes an electron injection layer, an electron transport layer, or a layer injecting electrons and transporting electrons simultaneously.

In an embodiment of the present invention, if the organic photoelectric device receives photons from an external light source, electrons and holes are generated between an electron donor and an electron acceptor. The holes produced are transported via an electron donor layer to an anode.

In an embodiment of the present invention, the organic photoelectric device may further include one or more photoactive layers selected from the group consisting of a hole injection layer, a hole transport layer, a hole blocking layer, a charge generating layer, an electron blocking layer, an electron injection layer and an electron transport layer.

In an embodiment of the present invention, in the organic photoelectric device, the cathode, the photoactive layer and the anode may be arranged in this order, or the anode, the photoactive layer and the cathode may be arranged in this order, without limitation.

In another embodiment, in the organic photoelectric device, the anode, the hole transport layer, the photoactive layer, the electron transport layer and the cathode may be arranged in this order, or the cathode, the electron transport layer, the photoactive layer, the hole transport layer and the anode may be arranged in this order, without limitation.

In another embodiment, a cathode buffer layer may be provided between the photoactive layer and the hole transport layer, or the photoactive layer and the electron transport layer. In this case, a hole injection layer may be further provided between the anode and the hole transport layer. In addition, an electron injection layer may be further provided between the cathode and the electron transport layer.

In an embodiment of the present invention, the photoactive layer includes one or two or more selected from the group consisting of an electron donor and acceptor.

In an embodiment of the present invention, the electron donor material may be selected from the group consisting of fullerene, fullerene derivatives, bathocuproine, semiconducting elements, semiconducting compounds and combinations thereof. Particularly, phenyl C61-butyric acid methyl ester (PC61BM) or phenyl C71-butyric acid methyl ester (PC71BM) may be used.

In an embodiment of the present invention, the electron donor and electron acceptor constitute a bulk hetero junction (BHJ). The electron donor material and the electron acceptor material may be mixed in a ratio of 1:10 to 10:1 (w/w).

In an embodiment of the present invention, the photoactive layer may have a bilayer structure including an n-type photoactive layer and a p-type photoactive layer.

In the present invention, the substrate may a glass substrate or a transparent plastic substrate, having excellent transparency, surface smoothness, tractability and water proof properties, but is not limited thereto, and any substrates commonly used in an organic photoelectric device may be used without limitation. Particularly, glass, polyethylene terephthalate (PET), polyethylene naphthalate (PEN), polypropylene (PP), polyimide (PI), triacetyl cellulose (TAC), etc., may be used, without limitation.

The anode electrode may be a material which is transparent and has excellent conductivity, but is not limited thereto. Metals such as vanadium, chromium, copper, zinc, and gold or alloys thereof; metal oxides such as zinc oxide, indium oxide, indium tin oxide (ITO), and indium zinc oxide (IZO); combinations of a metal and oxide such as ZnO:Al and SNO2:Sb; conductive polymers such as poly(3-methylthiophene), poly[3,4-(ethylene-1,2-dioxy)thiophene](PEDOT), polypyrrole and polyaniline, etc., may be used without limitation.

The method of forming the anode electrode is not specifically limited, but may include applying on one side of a substrate or coating into a film shape by using a sputtering, E-beam, thermal deposition, spin coating, screen printing, ink jet printing, doctor blade or gravure printing method.

If the anode electrode is formed on a substrate, a washing, removing moisture and modifying process into hydrophilic may be performed.

For example, an ITO substrate patterned is washed with a washing agent, acetone, isopropyl alcohol (IPA) one by one, and dried on a hot plate at 100-150° C. for 1-30 minutes, preferably, at 120° C. for 10 minutes to remove moisture, and after completely washing the substrate, the surface of the substrate is modified into hydrophilic.

Through the surface modification, a junction surface potential may be maintained to a level suitable to the surface potential of a photoactive layer. In addition, with the modification, the formation of a polymer thin film on the anode electrode may become easy, and the quality of a thin film may be improved.

As pre-treatment technique for the anode electrode, there are a) a surface oxidation method using parallel plate type electric discharge, b) a method of oxidizing surface through ozone produced using UV ultraviolet rays in a vacuum state, and c) an oxidizing method using oxygen radicals produced by plasma.

According to the state of the anode electrode or the substrate, one of the above-described methods may be selected. However, by any methods, it is commonly preferable that the detachment of oxygen at the surface of the anode electrode or substrate is prevented and the remain of moisture and organic materials is restrained maximally.

In a particular example, the method of oxidizing surface through ozone produced using UV may be used. In this case, after washing with ultrasonic waves, a patterned ITO substrate is baked on a hot plate and well-dried and then, injected into a chamber, and a UV lamp is operated to wash the patterned ITO substrate by ozone generated by the reaction of an oxygen gas with UV light.

However, the surface modification method of the patterned ITO substrate in the present invention is not specifically limited, and any methods of oxidizing a substrate may be applied.

The cathode electrode may be a metal having a low work function, but is not limited thereto. Particularly, metals such as magnesium, calcium, sodium, potassium, titanium, indium, yttrium, lithium, gadolinium, aluminum, silver, tin and lead, or alloys thereof; and materials with a multilayer structure such as LiF/Al, LiO2/Al, LiF/Fe, Al/Li, Al:BaF2, and Al:BaF2:Ba may be used, without limitation.

The cathode electrode may be formed through deposition in a thermal deposition apparatus showing a vacuum degree of $5 \times 10^{-7}$ torr or less, but is not limited to this method.

The hole transport layer and/or electron transport layer materials play the role of efficiently transporting electrons and holes separated from a photoactive layer to an electrode, and the material is not specifically limited.

The hole transport layer material may be PEDOT:PSS (Poly(3,4-ethylenediocythiophene) doped with poly(styrenesulfonic acid)), molybdenum oxide (MoOx); vanadium oxide (V2O5); nickel oxide (NiO); tungsten oxide (WOx), etc., without limitation.

The electron transport layer material may be electron-extracting metal oxides, particularly, metal complexes of 8-hydroxyquinoline; complexes including Alq3; metal complexes including Liq; LiF; Ca; titanium oxides (TiOx); zinc oxide (ZnO); cesium carbonate (Cs2CO3), etc., without limitation.

The photoactive layer may be formed by dissolving a photoactive material such as an electron donor and/or an electron acceptor in an organic solvent, and applying the solution by a method of spin coating, dip coating, screen printing, spray coating, doctor blade, brush painting, etc., but the method is not limited thereto.

In an aspect of the present invention, any one of the first electrode or the second electrode may be an ITO electrode, or the other one may be MoO3/Ag.

In an aspect of the present invention, if an organic solar cell is manufactured using the composition for a cathode buffer layer of the present invention, electron transfer between a photoactive layer and a cathode electrode is markedly increased in contrast to related arts. In addition, the photoelectric conversion efficiency (PCE) of an organic solar cell may be markedly increased by 8% or more, or 9% or more from this, the method may be used as an effective method for improving the efficiency of the organic solar cell in the technical art at this point.

In addition, in an aspect of the present invention, if an organic photodiode is manufactured using the cathode buffer composition of the present invention, leakage current may be markedly reduced. In addition, the leakage current of the organic photodiode may be reduced to 10-9 A/cm2 or less in the application conditions of a reverse voltage of −2 V, and accordingly, the method may be used as an effective method for improving the detectivity of the organic photodiode in the technical art at this point.

Further, the present invention provides a method of manufacturing an organic solar cell including: a step of preparing a mixture solution by mixing the compound represented by Formula 1 or stereoisomers thereof with a cathode buffer material; and a step of forming a layer using the mixture solution.

In the manufacturing method of the organic solar cell, the step of preparing a mixture solution by mixing the compound represented by Formula 1 or stereoisomers thereof with a cathode buffer material, should be understood as a particular embodiment suggested from the achievement of the better properties of an organic solar cell in devices manufactured by a method of mixing a cathode buffer material with the compounds of Preparation Examples 1-5 into a single layer not a double layer, based on the device property values measured from the organic solar cell devices of Examples 1-7 of the present invention, measured in Experimental Example 1.

In the present invention, in addition to the above-described method of preparing the mixture solution, the manufacture of a double layer including a layer using only a cathode material and a separate modification layer including the compound represented by Formula 1 or stereoisomers thereof, is shown in Examples 1-5.

Particularly, it is shown in the experimental examples that the excellent device properties of an organic solar cell are still achieved from the examples, and the manufacturing method of an organic solar cell includes the step of forming a double layer. Further, it could be understood as the manufacturing method of the present invention only if the step including the compound of Formula 1 or stereoisomers thereof of the present invention is included as a portion of the organic solar cell.

However, the step of preparing the mixture solution is the preparation method of an organic solar cell achieving better effects and is included as an aspect of the present invention.

Meanwhile, in the manufacturing method of the organic solar cell of the present invention, the step of forming a layer using the mixture solution may be understood as a step for forming a layer as a cathode buffer layer and is not specifically limited. However, in an aspect of the present invention, it should be understood that all kinds of layer forming methods commonly used may be included.

By using a composition for a cathode buffer layer including the compound represented by Formula 1 of the present invention, in order to experimentally measure power conversion efficiency in an organic photoelectric device, that is, an organic photoelectric device, a photoelectric conversion device, for example, an organic solar cell device, organic solar cell devices of Examples 1-7 were manufactured using the compounds of Preparation Examples 1-5, which are particular compounds of the present invention, and the photovoltaic properties thereof were evaluated through experiments. As a result, the compound represented by Formula 1 or stereoisomers thereof of the present invention are molecules having high dipole moment, and the electron transfer between a photoactive layer and a cathode electrode layer becomes smooth, and markedly high short circuit current (Jsc) and fill factor (FF) were shown. In conclusion, factors determining the device performance of an organic solar cell, Voc, Jsc and FF were all increased, and markedly high power conversion efficiency (PCE) was achieved (see Experimental Example 1 below).

Hereinafter, the present invention will be explained in detail referring to preparation examples, examples and experimental examples.

However, the preparation examples and experimental examples are only for illustrating the present invention, and the content of the present invention is not limited thereto.

<Preparation Example 1> Preparation of (E)-2-cyano-3-(1,1,7,7-tetramethyl-2,3,6,7-tetrahydro-1H, 5H-pyrido[3,2,1-ij]quinoline-9-yl)acrylic acid

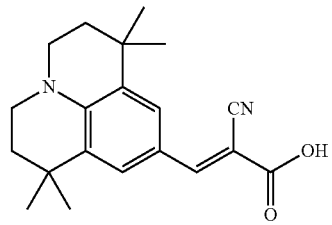 [SMILES: CC1(C)CCN2CCC(C)(C)c3cc(/C=C(\C#N)C(=O)O)cc1c32]

Step 1: Preparation of N,N-bis(3-methylbu-2-tene-1-yl) aniline

Aniline (20 g, 214 mmol) and calcium carbonate (11.8 g, 118 mmol) were put in DMF and stirred at 65° C. for 30 minutes. 1-chloro-3-methyl-2-butene (53 ml, 472 mmol) was slowly added thereto, followed by stirring at 80° C. for 40 minutes, and then the reaction mixture was cooled to room temperature. Then, a solid precipitated was filtered and washed with ether. The solid was dissolved in chloroform again, and the solution thus obtained was concentrated, and the solid thus produced was dissolved in a NaOH solution and extracted with ethyl acetate. An organic layer was dried with $MgSO_4$ and filtered, and solvent was removed to obtain the target compound of step 1, N,N-bis(3-methylbu-2-tene-1-yl)aniline (80%).

Step 2: Preparation of 1,1,7,7-tetramethyl-2,3,6,7-tetrahydro-1H,5H-pyrido[3,2,1-ij]quinolone The compound prepared in step 1 (33.4 g, 146 mmol) was added to $H_2SO_4$ at 0° C. and stirred at room temperature for 24 hours. Then, the reaction mixture was extracted using ethyl acetate and saturated $NaHCO_3$. An organic layer was dried with $MgSO_4$ and filtered, and solvent was removed. Then, by separating through column chromatography (MC:n-hexane=1:4), the target compound of step 2, 1,1,7,7-tetramethyl-2,3,6,7-tetrahydro-1H,5H-pyrido[3,2,1-ij]quinolone was obtained (17%).
$^1$H NMR (400 MHz, $CDCl_3$) δ 7.03 (d, J=7.6 Hz, 2H), 6.59 (t, J=7.6 Hz, 1H), 3.30-2.71 (m, 4H), 1.93-1.69 (m, 4H), 1.27 (s, 12H).

Step 3: Preparation of 1,1,7,7-tetramethyl-2,3,6,7-tetrahydro-1H,5H-pyrido[3,2,1-ij]quinolin-9-carboxaldehyde The compound prepared in step 2 (0.6 g, 2.62 mmol) was dissolved in DMF, and $POCl_3$ was added, followed by refluxing at 80° C. for 24 hours. Then, the reaction mixture was extracted with saturated $NaHCO_3$ and methylene chloride. An organic layer was dried with $MgSO_4$ and filtered, and solvent was removed. Then, by separating through column chromatography (MC:n-hexane=1:2), the target compound of step 3, 1,1,7,7-tetramethyl-2,3,6,7-tetrahydro-1H,5H-pyrido[3,2,1-ij]quinolin-9-carboxaldehyde was obtained (47%).
$^1$H NMR (300 MHz, $CDCl_3$) δ 9.64 (s, 1H), 7.55 (s, 2H), 3.43-3.04 (m, 4H), 1.84-1.65 (m, 4H), 1.30 (s, 17H).

Step 4: Preparation of (E)-2-cyano-3-(1,1,7,7-tetramethyl-2,3,6,7-tetrahydro-1H,5H-pyrido[3,2,1-ij]quinolin-9-yl)acrylic acid Under nitrogen, the compound prepared in step 3 (0.4 g, 1.55 mmol) and cyanoacetic acid (0.2 g, 2.41 mmol) were dissolved in ACN (5 ml) and CHCl$_3$ (5 ml). Then, piperidine (0.2 ml, 1.55 mmol) was added to the reaction solution, followed by stirring at 80° C. for 24 hours. After the reaction, a solid was precipitated using a HCl solution, and the solid thus precipitated was filtered and dried to obtain the final target compound, (E)-2-cyano-3-[1,1,7,7-tetramethyl-2,3,6,7-tetrahydro-1H,5H-pyrido[3,2,1-ij]quinolin-9-yl]acrylic acid (63%).
$^1$H NMR (400 MHz, CDCl$_3$) δ 8.03 (s, 1H), 7.82 (s, 2H), 3.43-3.24 (m, 4H), 1.88-1.57 (m, 4H), 1.31 (s, 12H).

<Preparation Example 2> Preparation of (Z)-2-cyano-3-(4-(diethylamino)phenyl)acrylic acid

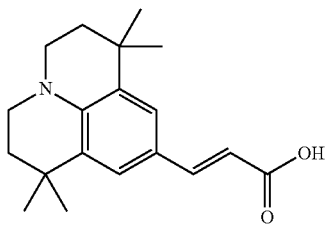 [SMILES: CC1(C)CCN2CCC(C)(C)c3cc(/C=C/C(=O)O)cc1c32]

The compound of Preparation Example 2 was prepared by performing a step of reacting the compound obtained by performing the same procedure to the step 3 in Preparation Example 1, and malonic acid as in step 3 of Preparation Example 5 below (71.4%).
$^1$H NMR (400 MHz, CDCl$_3$) δ 7.68 (d, J=15.7 Hz, 1H), 7.25 (s, 2H), 6.17 (d, J=15.7 Hz, 1H), 3.37-3.19 (m, 4H), 1.81-1.62 (m, 4H), 1.28 (s, 12H).

<Preparation Example 3> Preparation of (Z)-2-cyano-3-(4-(diethylamino)phenyl)acrylic acid

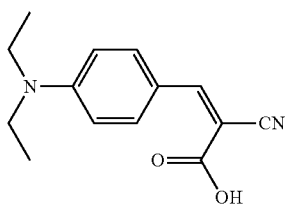

Step 1: Preparation of 4-(diethylamino)benzaldehyde

N,N-diethylaniline (0.93 g, 6.23 mmol) was added to DMF, and phosphoryl chloride (0.8 ml, 9.35 mmol) was slowly added. The reaction mixture was stirred at 80° C. for 24 hours. After the reaction, the reaction product was extracted with saturated Na$_2$CO$_3$ and methylene chloride. An organic layer was dried with MgSO$_4$ and filtered, and solvent was removed. Then, by separating through column chromatography (MC:n-hexane=1:2), the target compound of step 1, 4-(diethylamino)benzaldehyde was obtained (53%).
$^1$H NMR (400 MHz, CDCl$_3$) δ 9.70 (s, 1H), 7.71 (d, J=8.8 Hz, 2H), 6.68 (d, J=8.9 Hz, 2H), 3.44 (q, J=7.1 Hz, 4H), 1.23 (q, J=7.0 Hz, 7H).

Step 2: Preparation of (Z)-2-cyano-3-(4-(diethylamino)phenyl)acrylic acid

Under nitrogen, the compound prepared in step 1 (1.36 g, 7.67 mmol) and cyanoacetic acid (1.96 g, 23.02 mmol) were dissolved in ACN (30 ml). To the solution, piperidine (1.5 ml, 15.34 mmol) was added, followed by stirring at 80° C. for 24 hours. After the reaction, a solid was precipitated using a HCl solution, the solid thus precipitated was filtered and dried to obtain a final target compound, (Z)-2-cyano-3-(4-(diethylamino)phenyl)acrylic acid (65%).
$^1$H NMR (400 MHz, CDCl$_3$) δ 8.09 (s, 1H), 7.96 (d, J=8.9 Hz, 2H), 6.70 (d, J=9.1 Hz, 2H), 3.47 (q, J=7.1 Hz, 4H), 1.24 (t, J=7.1 Hz, 6H).

<Preparation Example 4> Preparation of (Z)-2-cyano-3-(4-(dibutylamino)phenyl)acrylic acid

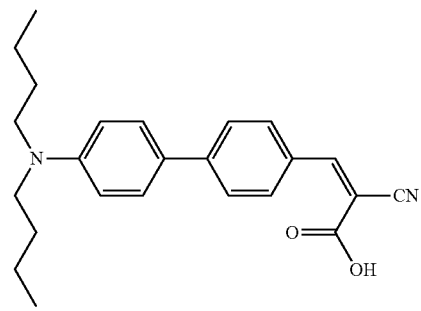 [SMILES: CCCCN(CCCC)c1ccc(-c2ccc(/C=C(/C#N)C(=O)O)cc2)cc1]

The compound of Preparation Example 4 was prepared by performing the same procedure in Preparation Example 3 except for using N,N-dibutylaniline instead of N,N-diethylaniline used in step 1 for preparing the compound of Preparation Example 3 (65%).
$^1$H NMR (400 MHz, CDCl$_3$) δ 8.10 (s, 1H), 7.96 (d, J=8.8 Hz, 2H), 6.73 (d, J=8.8 Hz, 2H), 3.48-3.14 (m, 4H), 1.73-1.54 (m, 4H), 1.41-1.28 (m, 4H), 0.98 (t, J=7.3 Hz, 6H).

<Preparation Example 5> Preparation of (E)-3-(4-(dioctylamino)phenyl)acrylic acid

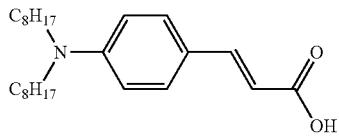

Step 1: Preparation of N,N-dioctylaniline

Aniline (4 g, 43 mmol) and potassium carbonate (24.9 g, 129 mmol) were added to DMF, 1-bromooctane (24.9 g, 129 mmol) was slowly added thereto, followed by reacting at 100° C. for 24 hours. After the reaction, the reaction product was extracted with water and ethyl acetate. An organic layer was dried with MgSO$_4$ and filtered, and solvent was removed. Through separating by column chromatography (MC:n-hexane=1:5), the target compound of step 1, N,N-dioctylaniline was obtained (97%).

Step 2: Preparation of 4-(dioctylamino)benzaldehyde

N,N-dioctylaniline (1.6 g, 3.29 mmol) prepared in step 1 was dissolved in DMF, and POCl$_3$ was added, followed by refluxing at 80° C. for 24 hours. After the reaction, the reaction product was extracted using NaHCO$_3$ and methylene chloride. An organic layer was dried with MgSO$_4$ and filtered, and solvent was removed. By separating through column chromatography (MC:n-hexane=1:2), the target compound of step 2, 4-(dioctylamino)benzaldehyde was obtained (68%).

$^1$H NMR (300 MHz, CDCl$_3$) δ 9.70 (s, 1H), 7.70 (d, J=8.8 Hz, 2H), 6.63 (d, J=8.9 Hz, 2H), 3.49-3.16 (m, 4H), 1.61 (s, 4H), 1.42-1.08 (m, 2H), 0.89 (t, J=5.8 Hz, 6H).

Step 3: Preparation of (E)-3-(4-(dioctylamino)phenyl)acrylic acid

Under nitrogen, the compound prepared in step 2 (0.77 g, 2.22 mmol) and malonic acid (0.46 g, 4.46 mmol) were dissolved in pyridine (24 ml). Piperidine (0.2 ml, 2.22 mmol) was added to the solution, and then stirred at 80° C. for 24 hours. After the reaction, a solid was precipitated with a HCl solution, the solid thus precipitated was filtered and dried to obtain a final target compound, (E)-3-(4-(dioctylamino)phenyl)acrylic acid (63%).

$^1$H NMR (400 MHz, CDCl$_3$) δ 7.69 (d, J=15.7 Hz, 1H), 7.40 (d, J=8.9 Hz, 2H), 6.59 (d, J=8.9 Hz, 2H), 6.18 (d, J=15.7 Hz, 1H), 3.38-3.08 (m, 4H), 1.59 (m, 4H), 1.40-1.13 (m, 2H), 0.89 (t, J=6.8 Hz, 6H).

<Preparation Example 6> Preparation of (E)-2-cyano-3-(4-(1,1,7,7-tetramethyl-2,3,6,7-tetrahydro-1H,5H-pyrido[3,2,1-ij]quinolin-9-yl)phenyl)acrylic acid

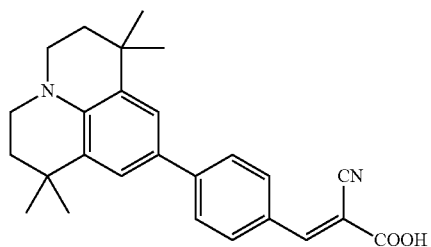 [SMILES: CC1(C)CCN2CCC(C)(C)c3cc(-c4ccc(/C=C(\C#N)C(=O)O)cc4)cc1c32]

The compound of Preparation Example 6 was prepared by performing the same synthetic method disclosed in RSC Advances, 2015, 5, 107540-107546.

$^1$H NMR (400 MHz, CD$_3$CN): 8.25 (s, 1H), 8.02 (d, J=8.4 Hz, 2H), 7.78 (d, J=8.8 Hz, 2H), 7.45 (s, 2H), 3.26 (t, J=6.0 Hz, 4H), 1.79 (t, J=6.0 Hz, 4H), 1.33 (s, 12H). MS (MALDI-TOF) m/z 400.44 (M+), calcd 400.51.

The chemical structures of the compounds prepared in Preparation Examples 1-6 are shown in Table 1 below.

TABLE 1

| | Structure |
|---|---|
| Preparation Example 1 | 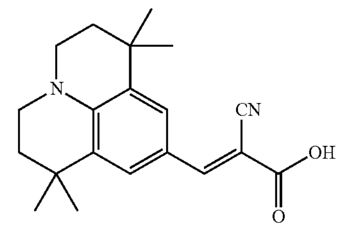 [SMILES: CC1(C)CCN2CCC(C)(C)c3cc(/C=C(\C#N)C(=O)O)cc1c32] |
| Preparation Example 2 | 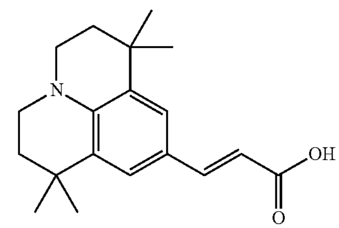 [SMILES: CC1(C)CCN2CCC(C)(C)c3cc(/C=C/C(=O)O)cc1c32] |
| Preparation Example 3 | 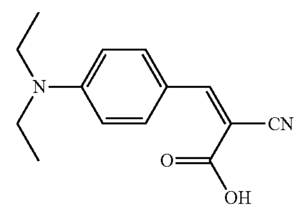 [SMILES: CCN(CC)c1ccc(/C=C(/C#N)C(=O)O)cc1] |
| Preparation Example 4 | 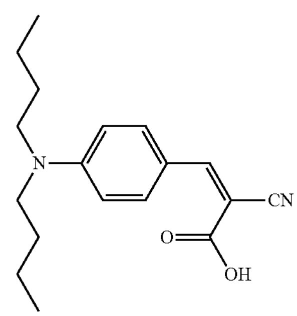 [SMILES: CCCCN(CCCC)c1ccc(/C=C(/C#N)C(=O)O)cc1] |
| Preparation Example 5 | 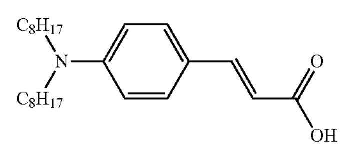 |
| Preparation Example 6 | 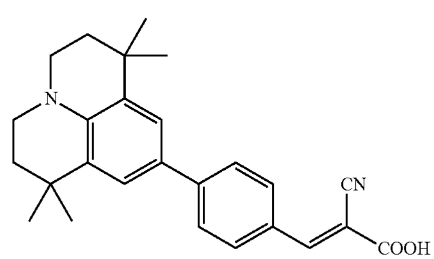 [SMILES: CC1(C)CCN2CCC(C)(C)c3cc(-c4ccc(/C=C(\C#N)C(=O)O)cc4)cc1c32] |

<Examples> Cathode Buffer Material-Applied Organic Solar Cell and Organic Photodiode In order to evaluate the performance of organic solar cells to which compounds for a buffer material having a dialkylaminophenyl group and cyanoacrylic acid and having high dipole moment of Preparation Examples 1-5 were applied, the compounds of Preparation Examples 1-5 were applied to organic solar cells having PTB7-Th:PC70BH, which is the conventionally typical polymer donor:acceptor and PPDT2FBT:PC70BM, which is known to have higher power conversion efficiency as photoactive layers, and these were compared and analyzed.

In addition, in order to evaluate the performance of an organic photodiode device to which the compound for a cathode buffer material of Preparation Example 1 of the present invention was applied, the compound of Preparation Example 1 was applied to an organic photodiode device having the conventional typical polymer donor:acceptor, PTB7:PC70BM as a photoactive layer, and this device was compared and analyzed.

<Example 1> Organic Solar Cell Applying the Buffer Material of Preparation Example 1

In order to manufacture an organic solar cell device applying the compound of Preparation Example 1 as a buffer material, on an indium tin oxide (ITO) glass, a ZnO layer was formed to a thickness of 30 nm using a ZnO sol-gel solution dissolved in an alcohol, Preparation Example 1 was dissolved in a THF solvent in 0.05 wt % concentration and spin coated at 4000 rpm for 30 seconds between the ZnO layer and a photoactive layer, and then, PTB7-Th:PC70BM (1:1.5) was dissolved in a chlorobenzene solvent in 12 mg/mL on the basis of a polymer donor, 3 vol % of diiodooctane (DIO) was added thereto as an additive, and the resultant solution was spin coated at 800 rpm for 15 seconds to form a thin film to a thickness of about 100 nm. After that, MoO3/Ag were deposited to a thicknesses of 7 nm and 120 nm, respectively, in a vacuum deposition apparatus with a vacuum degree of $3 \times 10^{-6}$ torr or less to manufacture an organic solar cell device.

<Example 2> Organic Solar Cell Applying the Buffer Material of Preparation Example 2

An organic solar cell device was manufactured by performing the same procedure as in Example 1 except for using the compound of Preparation Example 2 instead of the compound of Preparation Example 1 used in Example 1.

<Example 3> Organic Solar Cell Applying the Buffer Material of Preparation Example 3

An organic solar cell device was manufactured by performing the same procedure as in Example 1 except for using the compound of Preparation Example 3 instead of the compound of Preparation Example 1 used in Example 1.

<Example 4> Organic Solar Cell Applying the Buffer Material of Preparation Example 4

An organic solar cell device was manufactured by performing the same procedure as in Example 1 except for using the compound of Preparation Example 4 instead of the compound of Preparation Example 1 used in Example 1.

<Example 5> Organic Solar Cell Applying the Buffer Material of Preparation Example 5

An organic solar cell device was manufactured by performing the same procedure as in Example 1 except for using the compound of Preparation Example 5 instead of the compound of Preparation Example 1 used in Example 1.

<Example 6> Organic Solar Cell 2 Applying the Buffer Material of Preparation Example 1

First, a thin film of 30 nm was formed by spin coating a ZnO sol-gel solution obtained by mixing the compound of Preparation Example 1 in 0.1 wt % concentration between an indium tin oxide (ITO) layer and a photoactive layer, and then, PTB7-Th:PC70BM (1:1.5) was dissolved in a chlorobenzene solvent in 12 mg/mL on the basis of a polymer donor, 3 vol % of diiodooctane (DIO) was added thereto as an additive, and the resultant solution was spin coated at 800 rpm for 15 seconds to form a thin film to a thickness of about 100 nm. After that, MoO3/Ag were deposited in order to thicknesses of 7 nm and 120 nm, respectively, in a vacuum deposition apparatus with a vacuum degree of $3 \times 10^{-6}$ torr or less to manufacture an organic solar cell device.

<Example 7> Organic Solar Cell 3 Applying the Buffer Material of Preparation Example 1

An organic solar cell device was manufactured by performing the same procedure as in Example 6 except for using PPDT2FBT:PC70BM (Energy Envion. Sci., 2014, 7, 3040) as a photoactive layer, which is known to have further higher power conversion efficiency, instead of PTB7-Th:PC70BM (1:1.5) used in Example 6.

<Example 8> Organic Photodiode Applying the Buffer Material of Preparation Example 1

An organic photodiode device was manufactured by performing the same procedure as in Example 1 except for using PTB-7:PC70BM (1:1.5) as a photoactive layer instead of PTB7-Th:PC70BM (1:1.5) used in Example 1.

<Comparative Example 1> Organic Solar Cell not Applying Cathode Buffer Material

An organic solar cell device was manufactured by performing the same procedure as in Example 1 except for not using a compound for a buffer material.

<Comparative Example 2> Organic Solar Cell Applying the Buffer Material of Preparation Example 6

An organic solar cell device was manufactured by performing the same procedure as in Example 1 except for using the compound of Preparation Example 6 instead of the compound of Preparation Example 1 used in Example 1.

<Comparative Example 3> Organic Solar Cell 2 not Applying Cathode Buffer Material An organic solar cell device was manufactured by performing the same procedure as in Comparative Example 1 except for using PPDT2FBT:PC70BM (Energy Envion. Sci., 2014, 7, 3040) as a photoactive layer, which is known to have further higher power conversion efficiency, instead of PTB7-Th:PC70BM (1:1.5) used in Comparative Example 1.

<Comparative Example 4> Organic Photodiode not Applying Cathode Buffer Material

An organic photodiode device was manufactured by performing the same procedure as in Example 8 except for not using the compound of Preparation Example 1.

<Experimental Example 1> Evaluation of Optical Properties and Electrochemical Properties of the Compounds of Preparation Examples First, in order to evaluate the optical properties and electrochemical properties of the compounds of Preparation Examples 1-6, experiments were conducted as follows.

Particularly, UV/Vis absorption spectrum was measured for the compounds of Preparation Examples 1-5 in a THF solution state, which are compounds for a cathode buffer material of the present invention, and the compound of Preparation Example 6, which is the conventionally disclosed compound for a buffer material, and optical properties were evaluated. The results are shown in Table 2 below and FIG. 1.

Here, the absorption spectrum was obtained using a SHIMADZU/UV-2550 model UV-Visible spectrophotometer.

Meanwhile, in order to evaluate the electrochemical properties of the compounds of Preparation Examples 1-6, each compound was dissolved in a THF solvent, and electrochemical properties were measured through cyclic voltammetry (CV) using a Pt wire electrode in a solution phase. The measurement results are shown in Table 2 below and FIG. 2.

In this case, all measurements were calibrated with respect to the internal standard of ferrocene (Fc), and an ionization potential (IP) value was −4.8 eV with respect to a Fc/Fc+ oxidation-reduction system.

TABLE 2

| Preparation Example | Optical properties | | Electrochemical properties | | |
|---|---|---|---|---|---|
| | $\lambda_{max}$ (nm) | $E_g^{opt}$ (eV)$^{a)}$ | $E_{oxi/onset}$ (eV) | $HOMO_{elec}$ (eV)$^{b)}$ | LUMO (eV)$^{c)}$ |
| 1 | 467 | 2.66 | 0.446 | −5.15 | −2.49 |
| 2 | 371 | 3.03 | 0.523 | −5.22 | −2.19 |
| 3 | 453 | 2.74 | 0.619 | −5.32 | −2.58 |
| 4 | 512 | 2.42 | 0.415 | −5.12 | −2.70 |
| 5 | 364 | 3.11 | 0.536 | −5.24 | −2.12 |
| 6 | 451 | 2.05 | 0.30 | −5.05 | −3.00 |

(in Table 2,
$^{a)}$optical band gap, $E_g^{opt}$ = 1240/$\lambda$onset, film;
$^{b)}$HOMO = −[4.8 + ($E_{oxi}$ − $E_{Fc/Fc+}$) ] (eV); and
$^{c)}$LUMO = $E_g^{opt}$ + HOMO)

Referring to Table 1 and FIG. 1, it could be confirmed that the compounds of Preparation Examples 1-5 of the present invention absorbed light in a shorter wavelength region than the compound of Preparation Example 6, which was disclosed as the conventional cathode buffer layer material.

Accordingly, in case of the compounds of Preparation Examples 1-5 of the present invention, it could be found that the absorption in an absorption region by a photoactive layer might be further reduced, and further higher photoelectric current might be achieved.

Meanwhile, referring to Table 1 and FIG. 2, it was found that the HOMO level obtained through the oxidation potential values of the compounds of Preparation Examples 1-5 were −5.15 to −5.32 eV, which were deeper (lower) values than −5.05 eV of the compound of Preparation Example 6, and the values at the LUMO level obtained through an optical band gap using UV/Vis absorption spectrum were higher than the conventional compound of Preparation Example 6.

<Experimental Example 2> Evaluation of Performance of Cathode Buffer Layer

By using the compounds of Preparation Examples 1-5 of the present invention and the compound of Preparation Example 6 conventionally disclosed, improving effects of a cathode buffer material, for example, a ZnO layer were measured and evaluated as the performance of a cathode buffer layer.

Particularly, the work functions of thin films of ITO, ITO/ZnO and ITO/ZnO/compound of Preparation Example were measured using a UPS, and the thin film was formed by dissolving each compound of Preparation Examples 1-6 in a THF solvent in a concentration of 0.05 wt %/vol % and spin coating on the surface of ZnO.

The measurement results are shown in Table 3 below and FIG. 3.

TABLE 3

| Thin film | B.E. (eV) | WF (eV) |
|---|---|---|
| ITO | 16.77 | 4.45 |
| ZnO | 17.27 | 3.95 |
| ITO/ZnO/Preparation Example 1 | 17.74 | 3.48 |
| ITO/ZnO/Preparation Example 2 | 17.84 | 3.38 |
| ITO/ZnO/Preparation Example 3 | 18.04 | 3.18 |
| ITO/ZnO/Preparation Example 4 | 17.49 | 3.73 |
| ITO/ZnO/Preparation Example 5 | 18.22 | 3.00 |
| ITO/ZnO/Preparation Example 6 | 17.08 | 3.26 |

(in Table 3,
B.E. (eV): binding energy (eV), and
WF (eV): ΔE (21.22 eV) − B.E. (eV))

Referring to Table 3 and FIG. 3, the work function of ITO (−4.45 eV) was changed to −3.95 eV in conditions of ITO/ZnO, increased to −3.26 eV in case of stacking Preparation Example 6, and increased to −3.48, −3.38, −3.18, −3.73, and −3.00 eV for cases of stacking Preparation Examples 1, 2, 3, 4, and 5, respectively. Through this, it could be found that the compound for a cathode buffer material of the present invention even further improved the work function of the ZnO layer and contributed to the increase of the electron extraction properties of an organic photoelectric device.

<Experimental Example 3> Evaluation of Performance of Organic Solar Cell

Experiments for evaluating the performance of the organic solar cell devices of Examples 1-10 and Comparative Examples 1-3 were conducted.

Particularly, $V_{oc}$(V) and $J_{sc}$ (mA/cm$^2$) of each of the organic solar cell devices were obtained by computing a voltage value when current was 0 and a current value when voltage was 0 referring to the current-voltage curves of the devices manufactured (see FIG. 3 and FIG. 4), and fill factor (FF) was obtained by computing from the following Mathematical Formula 1:

$$FF = V_{mpp} \cdot J_{mpp}/V_{oc} \cdot J_{sc} \quad \text{[Mathematical Formula 1]}$$

(in Mathematical Formula 1,
$V_{mmp}$ and $J_{mpp}$ represent voltage and current values, respectively, at a point showing maximum power when measuring the current-voltage of the device manufactured, and $V_{oc}$(V) and $J_{sc}$ (mA/cm$^2$) represent a voltage value when current was 0 and a current value when voltage was 0, respectively, in the current-voltage curves of the device manufactured)

Further, photoelectric conversion efficiency (%) was obtained by computing from the following Mathematical Formula 2:

$$PCE \text{ (photoelectric conversion efficiency,%)} = 100 \times FF \times V_{oc} \cdot J_{sc}/P_{in} \quad \text{[Mathematical Formula 2]}$$

(in Mathematical Formula 2,

FF, $V_{oc}$ and $J_{sc}$ are the same as defined in Mathematical Formula 1, and $P_{in}$ represents total energy of light incident to a device)

By performing as described above, measurement values on the devices of Examples 1-7 and Comparative Examples 1-3 are shown in Table 4 below and FIG. 3 and FIG. 4.

TABLE 4

| | Photoactive layer | Cathode buffer layer | $V_{oc}$ (V) | $J_{sc}$ (mA/cm$^2$) | FF (%) | PCE (%) |
|---|---|---|---|---|---|---|
| Example 1 | PTB7-Th:PC70BM | Double layer of ZnO/Preparation Example 1 | 0.82 | 16.40 | 66.3 | 8.87 |
| Example 2 | PTB7-Th:PC70BM | Double layer of ZnO/Preparation Example 2 | 0.81 | 15.89 | 66.1 | 8.51 |
| Example 3 | PTB7-Th:PC70BM | Double layer of ZnO/Preparation Example 3 | 0.82 | 15.93 | 66.3 | 8.58 |
| Example 4 | PTB7-Th:PC70BM | Double layer of ZnO/Preparation Example 4 | 0.82 | 16.43 | 65.4 | 8.66 |
| Example 5 | PTB7-Th:PC70BM | Double layer of ZnO/Preparation Example 5 | 0.82 | 16.24 | 66.2 | 8.69 |
| Example 6 | PTB7-Th:PC70BM | Mixture layer of ZnO + Preparation Example 1 | 0.80 | 16.75 | 68.0 | 9.18 |
| Example 7 | PPDT2FBT:PC70BM | Mixture layer of ZnO + Preparation Example 1 | 0.78 | 17.75 | 70.4 | 9.71 |
| Comparative Example 1 | PTB7-Th:PC70BM | Single layer of ZnO | 0.81 | 15.32 | 57.8 | 7.18 |
| Comparative Example 2 | PTB7-Th:PC70BM | ZnO/Preparation Example 6 | 0.81 | 16.34 | 62.0 | 8.17 |
| Comparative Example 3 | PPDT2FBT:PC70BM | Single layer of ZnO | 0.77 | 16.51 | 69.0 | 8.81 |

As confirmed from Table 4, the organic solar cell devices with a reverse structure based on PTB7-Th:PC70BM, the devices forming a double layer of the cathode buffer layer materials of Preparation Examples 1-5 of the present invention and a ZnO layer showed higher conversion efficiency than the device applying a buffer layer formed as the conventional ZnO single layer (Comparative Example 1). In addition, the device manufactured by mixing the compound of Preparation Example 1 of the present invention by the preparation process of a ZnO sol-gel solution (Example 6) was confirmed to show higher conversion efficiency than the conventional ZnO single layer. Further, for an organic solar cell device with a reverse structure based on PPDT2FBT:PC70BM, the device of Example 7 of the present invention was also confirmed to show better photoelectric conversion efficiency than Comparative Example 3.

Meanwhile, as shown in Example 1 to Example 5, the devices applying Preparation Examples 1-5 of the present invention were confirmed to show better performance of an organic solar cell device when compared with the device applying Preparation Example 6, which is reported in the conventional document (Comparative Example 2).

It could be found that the compound for a cathode buffer of the present invention has a condensed structure when compared with the compound of Preparation Example 6 and is a compound having higher dipole moment, and accordingly, achieves easier electron extraction between a photoactive layer and an ITO transparent electrode and excellent device efficiency.

On the other hand, from the FF values of Examples 1-5 of the present invention, it could be found that the compounds of Preparation Examples 1-5 provided as particular embodiments of the present invention may improve the FF of an organic photoelectric device, for example, an organic solar cell, and accordingly may achieve improving effects of power conversion efficiency and improving of the shunt resistance of a device, thereby accomplishing the improving effects of the stability of a device.

On the other hand, it could be confirmed that though the cathode buffer layer was formed as a mixture single layer not as a double layer as in Examples 6 and 7, still excellent photoelectric conversion efficiency was achieved.

From the results, in applying the compound for a cathode buffer of the present invention to an organic photoelectric device, the formation of a single layer may be more useful in a printing process when compared with the formation of a double layer.

<Experimental Example 4> Evaluation of Properties of Organic Photodiode

Experiments on the evaluation of the performance of the organic photodiode devices of Example 8 and Comparative Example 4 were conducted.

Particularly, both Example 8 and Comparative Example 4 have a device structure of ITO/ZnO/PTB-7:PC70BM (1:1.5)/MoO3/Ag, where Example 8 used the compound of Preparation Example 1 as a cathode buffer layer and a double layer with ZnO, and Comparative Example 4 used only a ZnO single layer. Meanwhile, experiment on the J-V properties of a device was conducted in a photoconductive mode, because signal linearity is increased when a reverse bias reduces signal response time and the intensity of light is increased, and the current density (mA/cm$^2$)-voltage (V) property values of the devices manufactured through Example 8 and Comparative Example 4 are shown in FIG. 6 and FIG. 7, respectively. The responsivity and detectivity of a photo detecting device are the function of voltage and light intensity and are obtained by the measurement between −2 V to +2 V in accordance with the change of light intensity from J-V properties. Resultant values of the devices manufactured through Example 8 and Comparative Example 4 are summarized and shown in Table 5 and Table 6 below.

TABLE 5

| P (μW) | P (W/cm$^2$) | $J_D$ (A/cm$^2$) | $J_{Ph}$ (A/cm$^2$) | Responsivity at 530 nm (A/W) | Detectivity at 530 nm (Jones) |
|---|---|---|---|---|---|
| Light intensity (power supply): −2 V | | | | | |
| 0 | 0.00E+00 | 2.27E−08 | 2.27E−08 | — | — |
| 5 | 5.56E−05 | 2.27E−08 | 1.67E−05 | 0.30 | 3.52E+12 |
| 30 | 3.33E−04 | 2.27E−08 | 9.90E−05 | 0.30 | 3.48E+12 |
| 100 | 1.11E−03 | 2.27E−08 | 3.05E−04 | 0.27 | 3.22E+12 |
| 200 | 2.22E−03 | 2.27E−08 | 5.97E−04 | 0.27 | 3.15E+12 |
| 400 | 4.44E−03 | 2.27E−08 | 1.20E−03 | 0.27 | 3.17E+12 |
| Light intensity (power supply): −1 V | | | | | |
| 0 | 0.00E+00 | 5.29E−09 | 5.29E−09 | — | — |
| 5 | 5.56E−05 | 5.29E−09 | 1.61E−05 | 0.29 | 7.03E+12 |
| 30 | 3.33E−04 | 5.29E−09 | 9.68E−05 | 0.29 | 7.06E+12 |
| 100 | 1.11E−03 | 5.29E−09 | 2.99E−04 | 0.27 | 6.54E+12 |
| 200 | 2.22E−03 | 5.29E−09 | 5.84E−04 | 0.26 | 6.39E+12 |
| 400 | 4.44E−03 | 5.29E−09 | 11.8E−03 | 0.27 | 6.45E+12 |
| Light intensity (power supply): −0.5 V | | | | | |
| 0 | 0.00E+00 | 2.22E−09 | 2.22E−09 | — | — |
| 5 | 5.56E−05 | 2.22E−09 | 1.59E−05 | 0.29 | 1.07E+13 |
| 30 | 3.33E−04 | 2.22E−09 | 9.49E−05 | 0.28 | 1.07E+13 |
| 100 | 1.11E−03 | 2.22E−09 | 2.94E−04 | 0.26 | 9.92E+13 |
| 200 | 2.22E−03 | 2.22E−09 | 5.73E−04 | 0.26 | 9.68E+13 |
| 400 | 4.44E−03 | 2.22E−09 | 1.16E−03 | 0.26 | 9.80E+13 |
| Light intensity (power supply): 0 V | | | | | |
| 0 | 0.00E+00 | 3.36E−10 | 3.36E−10 | — | — |
| 5 | 5.56E−05 | 3.36E−10 | 1.50E−05 | 0.27 | 2.60E+13 |
| 30 | 3.33E−04 | 3.36E−10 | 9.15E−05 | 0.27 | 2.64E+13 |
| 100 | 1.11E−03 | 3.36E−10 | 2.83E−04 | 0.26 | 2.46E+13 |
| 200 | 2.22E−03 | 3.36E−10 | 5.53E−04 | 0.25 | 2.40E+13 |
| 400 | 4.44E−03 | 3.36E−10 | 1.12E−03 | 0.25 | 2.43E+13 |

TABLE 6

| P (μW) | P (W/cm$^2$) | $J_D$ (A/cm$^2$) | $J_{Ph}$ (A/cm$^2$) | Responsivity at 530 nm (A/W) | Detectivity at 530 nm (Jones) |
|---|---|---|---|---|---|
| Light intensity (power supply): −2 V | | | | | |
| 0 | 0.00E+00 | 1.11E−07 | 1.11E−07 | — | — |
| 5 | 5.56E−05 | 1.11E−07 | 1.56E−05 | 0.28 | 1.49E+12 |
| 30 | 3.33E−04 | 1.11E−07 | 8.92E−05 | 0.27 | 1.42E+12 |
| 100 | 1.11E−03 | 1.11E−07 | 2.90E−04 | 0.26 | 1.38E+12 |
| 200 | 2.22E−03 | 1.11E−07 | 5.77E−04 | 0.26 | 1.38E+12 |
| 400 | 4.44E−03 | 1.11E−07 | 1.13E−03 | 0.25 | 1.35E+12 |
| Light intensity (power supply): −1 V | | | | | |
| 0 | 0.00E+00 | 3.58E−08 | 3.58E−08 | — | — |
| 5 | 5.56E−05 | 3.58E−08 | 1.50E−05 | 0.27 | 2.53E+12 |
| 30 | 3.33E−04 | 3.58E−08 | 8.59E−05 | 0.26 | 2.41E+12 |
| 100 | 1.11E−03 | 3.58E−08 | 2.80E−04 | 0.25 | 2.36E+12 |
| 200 | 2.22E−03 | 3.58E−08 | 5.59E−04 | 0.25 | 2.35E+12 |
| 400 | 4.44E−03 | 3.58E−08 | 1.09E−03 | 0.25 | 2.29E+12 |
| Light intensity (power supply): −0.5 V | | | | | |
| 0 | 0.00E+00 | 1.69E−08 | 1.69E−08 | — | — |
| 5 | 5.56E−05 | 1.69E−08 | 1.44E−05 | 0.26 | 3.53E+12 |
| 30 | 3.33E−04 | 1.69E−08 | 8.33E−05 | 0.25 | 3.40E+12 |
| 100 | 1.11E−03 | 1.69E−08 | 2.72E−04 | 0.24 | 3.33E+12 |
| 200 | 2.22E−03 | 1.69E−08 | 5.43E−04 | 0.24 | 3.32E+12 |
| 400 | 4.44E−03 | 1.69E−08 | 1.06E−03 | 0.24 | 3.24E+12 |
| Light intensity (power supply): 0 V | | | | | |
| 0 | 0.00E+00 | 9.92E−10 | 9.92E−10 | — | — |
| 5 | 5.56E−05 | 9.92E−10 | 1.31E−05 | 0.24 | 1.32E+13 |
| 30 | 3.33E−04 | 9.92E−10 | 7.69E−05 | 0.23 | 1.29E+13 |
| 100 | 1.11E−03 | 9.92E−10 | 2.52E−04 | 0.23 | 1.27E+13 |
| 200 | 2.22E−03 | 9.92E−10 | 5.03E−04 | 0.23 | 1.27E+13 |
| 400 | 4.44E−03 | 9.92E−10 | 9.80E−04 | 0.22 | 1.23E+13 |

(the responsivity may be simply obtained from output current density divided by input light power (light intensity))

As shown in FIG. 6 and FIG. 7, the current density was linearly increased in accordance with the increase of input light intensity, and the device of Example 8 and the device of Comparative Example 4 showed about 0.27-0.28 and 0.25-0.27 A/W in various light intensities, respectively. The device applying the cathode buffer material of the present invention (Example 8) showed better results.

In conclusion, the compounds of Preparation Examples 1-5 of the present invention showed very stable responsivity as the function of light intensity and driving voltage, and this may be favorable in obtaining uniform signal detection.

As shown in the following Mathematical Formula 3, the responsivity has correlation with dark current density (Jd):

$$R(\lambda)=I_{PH}/P \cdot [A/W]$$ [Mathematical Formula 3]

(in Mathematical Formula 3,
R is responsivity,
P is the intensity of light exposed, and
$I_{PH}$ means generated photoelectric current)

Accordingly, the responsivity means the ratio of photoelectric current value produced against the quantity of light exposed.

Meanwhile, the detectivity may be obtained by the following Mathematical Formula 4:

$$D^*=R/(2qJ_d)^{0.5} \cdot [cm(Hz)^{1/2}/W]$$ [Mathematical Formula 4]

(in Mathematical Formula 4,
D* is detectivity,
R is responsivity of Mathematical Formula 3,
q is the absolute electric charge of electrons, $1.6 \times 10^{-19}$ C, and
$J_d$ means current density (dark current density, A/cm$^2$) in conditions of not getting light)

Meanwhile, the response properties could not exceed a reaction value and have maximum limit because calculated on the assumption that the external quantum efficiency was 100%.

Accordingly, the best method of increasing the detectivity is minimizing the dark current.

As shown in Table 5 and FIG. 6, the device of Example 8 has dark current densities of $5.29 \times 10^{-9}$ A/cm$^2$ and $2.27 \times 10^{-8}$ A/cm$^2$ in reverse voltage application conditions of −1 V and −2 V, respectively. If the responsivity and the detectivity are calculated through Mathematical Formulae 3 and 4, 0.3 A/W and $3.5 \times 10^{12}$ Jones were obtained, respectively.

On the contrary, as shown in Table 6 and FIG. 7, the device of Comparative Example 4 showed dark current densities of $3.58 \times 10^{-8}$ A/cm$^2$ and $1.11 \times 10^{-7}$ A/cm$^2$ in reverse voltage application conditions of −1 V and −2 V, respectively, and was confirmed to have 10 times or higher values when compared with the device of Example 8. If the responsivity and the detectivity are calculated therefrom, 0.28 A/W and $1.49 \times 10^{12}$ Jones were obtained, respectively, and were inferior to the device of Example 8.

Likewise, an organic photodiode device applying the compound for a cathode buffer material of the present invention provides lower dark current density and higher photoelectric efficiency through the interface control between a cathode electrode and a photoactive layer and may obtain excellent responsivity and detectivity when compared with a device applying the conventional cathode buffer material, and accordingly, it could be confirmed that it serves the improvement of the performance of an organic photodiode.

Therefore, the compound for a cathode buffer of the present invention may be used as a material for a cathode buffer in an organic photoelectric device, for example, an organic solar cell device and an organic photodiode device, to improve the power conversion efficiency of the device, minimize leakage current, improve the shunt resistance of the device, and achieve the effects of improving device stability, and thus, is industrially useful. In addition, excellent photoelectric conversion efficiency may be achieved for both cases of applying the compound for a cathode buffer of the present invention to a double layer or a single layer by mixing, and the compound for a cathode buffer of the present invention has advantages of easy application to a printing process and is industrially applicable.

INDUSTRIAL APPLICABILITY

When the novel compound of the present invention is applied to a cathode buffer layer of an organic photoelectric device, for example, an organic solar cell or an organic photodiode, there is an effect in which the surface characteristics of an electron transport layer are improved through the high dipole moment of the novel compound to thereby facilitate electron extraction from a photoactive layer to a cathode electrode and to reduce series resistance and leakage current, and accordingly, the performance of an organic photoelectric device (organic solar cell, organic photodiode, etc.) to be manufactured may be remarkably improved, which is industrially advantageous.

The invention claimed is:
1. An organic photoelectric device comprising:
a first electrode;
a second electrode oppositely provided to the first electrode;
a photoactive layer provided between the first electrode and the second electrode; and
a cathode buffer layer provided between the photoactive layer and the first electrode or between the photoactive layer and the second electrode,
wherein the photoactive layer comprises a donor comprising a polymer and an acceptor comprising fullerene, and
wherein the cathode buffer layer comprises:
a compound according to Formula 1, or a stereoisomer thereof; and
one or more cathode buffer materials selected from the group consisting of an n-type metal oxide, a transition metal chelate, and an alkali metal compound,

[Formula 1]

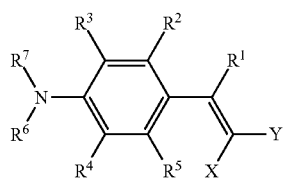

wherein:
X is $CO_2H$;
Y is hydrogen or CN;
$R^1$ is hydrogen;
$R^2$ and $R^5$ are each independently H;
$R^3$ is H or, together with $R^7$, forms a 6-member heterocyclic nitrogenous ring substituted with dimethyl;
$R^4$ is H or, together with $R^6$, forms a 6-member heterocyclic nitrogenous ring substituted with dimethyl;
$R^6$ is $C_{2-8}$ alkyl, or, together with $R^4$, forms a 6-member heterocyclic nitrogenous ring substituted with dimethyl; and
$R^7$ is $C_{2-8}$ alkyl, or, together with $R^3$, forms a 6-member heterocyclic nitrogenous ring substituted with dimethyl.

2. The organic photoelectric device according to claim 1, wherein the compound or stereoisomers thereof are mixed with and dispersed in the cathode buffer material.

3. The organic photoelectric device according to claim 1, wherein the cathode buffer layer for an organic photoelectric device comprises:
a first layer comprising the cathode buffer material; and
a second layer comprising the compound or stereoisomer thereof.

4. The organic photoelectric device according to claim 1, wherein the one or more cathode buffer materials comprises ZnO.

5. The organic photoelectric device according to claim 1, wherein:
$R^6$ is $C_{2-8}$ alkyl; and
$R^7$ is $C_{2-8}$ alkyl.

6. The organic photoelectric device according to claim 1, wherein:
$R^6$, together with $R^4$, forms a 6-member heterocyclic nitrogenous ring substituted with dimethyl; and
$R^7$, together with $R^3$, forms a 6-member heterocyclic nitrogenous ring substituted with dimethyl.

7. The organic photoelectric device according to claim 1, wherein:
$R^6$, together with $R^4$, forms

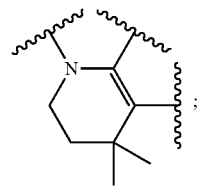 [SMILES: *C1=C(*)C(C)(C)CCN1*]

and $R^7$, together with $R^3$, forms

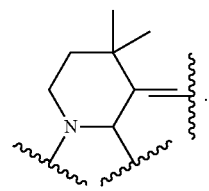

8. The organic photoelectric device according to claim 1, wherein the compound represented by Formula 1 is selected from the group consisting of
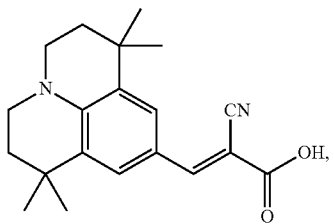
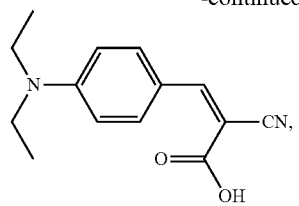
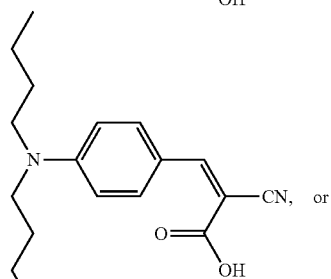
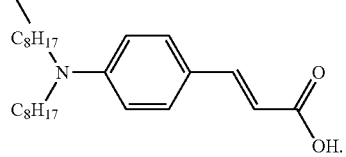
* * * * *